(12) United States Patent
Geddes et al.

(10) Patent No.: US 8,114,598 B2
(45) Date of Patent: Feb. 14, 2012

(54) HIGH-SENSITIVITY ASSAYS FOR PATHOGEN DETECTION USING METAL ENHANCED FLUORESCENCE

(75) Inventors: Chris D. Geddes, Bel-Air, MD (US); Joseph R. Lakowitz, Ellicott City, MD (US); Leslie W. J. Baillie, Columbia, MD (US)

(73) Assignee: University of Maryland, Baltimore County, Baltimore, MD (US)

( * ) Notice: Subject to any disclaimer, the term of this patent is extended or adjusted under 35 U.S.C. 154(b) by 914 days.

(21) Appl. No.: 10/536,502

(22) PCT Filed: Nov. 26, 2003

(86) PCT No.: PCT/US03/38163
§ 371 (c)(1),
(2), (4) Date: Dec. 14, 2005

(87) PCT Pub. No.: WO2004/059279
PCT Pub. Date: Jul. 15, 2004

(65) Prior Publication Data
US 2006/0147927 A1    Jul. 6, 2006

Related U.S. Application Data

(60) Provisional application No. 60/429,263, filed on Nov. 26, 2002.

(51) Int. Cl.
*C12Q 1/68* (2006.01)
*C07H 21/04* (2006.01)
(52) U.S. Cl. ............... 435/6.11; 435/6.15; 536/24.32
(58) Field of Classification Search .............. None
See application file for complete search history.

(56) References Cited

U.S. PATENT DOCUMENTS

| | | | |
|---|---|---|---|
| 5,017,009 A | 5/1991 | Schutt et al. | |
| 5,449,918 A | 9/1995 | Krull et al. | |
| 5,814,516 A | 9/1998 | Vo-Dinh | |
| 5,830,769 A | 11/1998 | Wieder et al. | |
| 5,854,008 A | 12/1998 | Diamandis | |
| 5,866,433 A | 2/1999 | Schalkhammer et al. | |
| 6,207,369 B1 * | 3/2001 | Wohlstadter et al. | 435/6 |
| 6,214,628 B1 | 4/2001 | Lakowicz et al. | |
| 6,369,206 B1 | 4/2002 | Leone et al. | |
| 6,699,717 B1 | 3/2004 | Rao et al. | |
| 6,770,488 B1 * | 8/2004 | Carron et al. | 436/525 |
| 7,095,502 B2 | 8/2006 | Lakowicz et al. | |
| 7,253,452 B2 | 8/2007 | Steckel et al. | |
| 7,348,182 B2 | 3/2008 | Martin et al. | |
| 7,351,590 B2 | 4/2008 | Martin | |
| 7,718,445 B2 | 5/2010 | Martin | |
| 2002/0045268 A1 | 4/2002 | Lakowicz et al. | |
| 2002/0160400 A1 | 10/2002 | Lakowicz | |
| 2003/0087297 A1 | 5/2003 | Ootsubo et al. | |
| 2003/0228682 A1 | 12/2003 | Lakowicz et al. | |
| 2004/0160606 A1 | 8/2004 | Lakowicz et al. | |
| 2005/0053974 A1 | 3/2005 | Lakowicz et al. | |
| 2005/0202464 A1 | 9/2005 | Lakowicz | |
| 2005/0226129 A1 | 10/2005 | Carr | |
| 2006/0147927 A1 | 7/2006 | Geddes et al. | |
| 2006/0256331 A1 | 11/2006 | Lakowicz et al. | |

FOREIGN PATENT DOCUMENTS

| | | |
|---|---|---|
| EP | 0079139 | 5/1983 |
| WO | 89/09408 | 10/1989 |
| WO | WO 9727317 A1 * | 7/1997 |
| WO | 99/44045 | 9/1999 |
| WO | WO 0109388 | 7/2000 |
| WO | 03/027678 | 4/2003 |
| WO | WO 2004/024191 | 3/2004 |

OTHER PUBLICATIONS

Malicka et al., "Effects of metallic silver particles on resonance energy transfer in labeled bovine serum albumin," Biochem. Biophys. Res. Comm., Jun. 2002, vol. 294, pp. 886-892.*

Cao et al., "Nanoparticles within Raman Spectroscopic Fingerprints for DNA and RNA Detection," Science, Aug. 2002, vol. 297, pp. 1536-1540.*

Qi et al. Utilization of the rpoB gene as a specific chromosomal marker for real-time PCR detection of *Bacillus anthracis*. Applied and Environmental Microbiology (2001) 67(8): 3720-3727.*

Letuta et al. Photochromic transformations in doped polymers upon two-photon excitation. Quantum Electronics (2001) 31(10): 925-928.*

Doukas et al. Fluorescence quantum yield of visual pigments: Evidence for subpicosecond isomerization rates. Proceedings of the National Academy of Sciences, USA (1984) 81: 4790-4794.*

Malicka et al. Fluorescence spectral properties of cyanine dye labeled DNA near metallic silver particles. Biopolymers (2003) 72(2): 96-104.*

Lukomska et al. Two-photon induced fluorescence of Cy5-DNA in buffer solution and on silver island films. Biochemical and Biophysical Research Communications (2005) 328: 78-84.*

(Continued)

*Primary Examiner* — Young J Kim
*Assistant Examiner* — Angela M Bertagna
(74) *Attorney, Agent, or Firm* — Marianne Fuierer; Moore & Van Allen, PLLC

(57) ABSTRACT

The present invention relates to an assay including a surface having silver colloids or islands attached thereto. Attached to the surface and/or silver colloids/islands are polynucleotides which are complimentary to a target polynucleotide sequence. The assay is performed by adding the target polynucleotide sequence to the assay surface and allowed to hybridize with the capture polynucleotides. Fluorophore-labeled capture polynucleotides are added and hybridize to the target polynucleotide. Bound target polynucleotides are detected by metal enhanced fluorescence.

21 Claims, 16 Drawing Sheets

OTHER PUBLICATIONS

Cao et al. DNA-Modified Core-Shell Ag/Au Nanoparticles. Journal of the American Chemical Society (Jul. 2001) 123: 7961-7962.*

Gryczynski et al. Intensified flurorescence. Photonics Spectra (Oct. 2001) 35(10): 96, 97, 99-102, 104.*

Shuming Nie et al.; Probing Single Molecules and Single Nanoparticles by Surface-Enhanced Raman Scattering; Science; Feb. 21, 1997; pp. 1102-1108; vol. 275; USA.

Joseph R. Lakawicz et al.; Intrinsic Fluorescence from DNA Can Be Enhanced by Metallic Particles; Biochemical and Biophysical Research Communications; 2001; pp. 875-879; 286; Academic Press; USA.

Friedlander, A. M.; Anthrax: Clinical Features, Pathogenesis, and Potential Biological Warfare Threat; Current Clinical Topics in Infectious Diseases; 2000; pp. 335-349; (eds. Reminton, J S. & Schwartz, M. N.) Blackwell Science, Inc., Malden, MA.

Kummerlen, J. et al.; Enhanced dye fluorescence over silver island films: analysis of the distance dependence; Molecular Physics; 1993; pp. 1031-1046; vol. 80, No. 5.

Xu, c. and Webb, W. W.; Multiphoton Excitation of Molecular Fluorophores and Nonlinear Laser Microscopy; Topics in Fluorescence Spectroscopy: Nonlinear and Two-Photon-Induced Fluorescence; 1997; pp. 471-540; vol. 5; Plenum Press, New York (ed. J. Lakowicz).

Weitz, D. A. et al.; Fluorescent lifetimes of molecules on silver-island films; Optics Letters; Feb. 1982; pp. 89-91; vol. 7, No. 2.

Glass, A. M. et al.; Interaction of metal particles with adsorbed dye molecules: absorption and luminescence; Optics Letters; Sep. 1980; pp. 368-370; vol. 5, No. 9.

Kreibig, U. and Genzel, L.; Optical Absorption of Small Metallic Particles; Surface Science; 1985; pp. 678-700; vol. 156; North-Holland, Amsterdam.

Pastoriza-Santos, i. and Liz-Marzan, L. M.; Reduction of silver nanoparticles in DMF. Formation of monolayers and stable colloids.; Pure Appl. Chem.; 2000; pp. 83-90; vol. 72, Nos. 1-2.

Turnbull, P. C. B. et al.; *Bacillus anthracis* but not always anthrax; Journal of Applied Bacteriology; 1992; pp. 21-28; vol. 72.

Farmer, S. C. and Patten, T. E.; Synthesis of Luminescent Organic/Inorganic Polymer Nanocomposites; Polym. Mater. Sci. Eng.; 2000; pp. 237-238; vol. 82.

Yang, C.-C. et al.; Deposition of Ultrathin Films by a Withdrawal Method; Thin Solid Films; 1980; pp. 117-127; vol. 74; printed in the Netherlands.

Grabar, K. C. et al.; Preparation and Characterization of Au Colloid Monolayers; Anal. Chem.; 1995; pp. 735-743; vol. 67.

Mullis, K. B.; Target amplification for DNA analysis by the polymerase chain reaction; Ann. Biol. Clin.; 1990; pp. 579-582; vol. 48.

Hayakawa, T. et al.; Field enhancement effect of small Ag particles on the fluorescence from Eu3+-doped SiO2 glass; Applied Physics Letters; Mar. 1999; pp. 1513-1515; vol. 74, No. 11.

Welkos, S. L. et al.; Sequence and analysis of the DNA encoding protective antigen of *Bacillus anthracis*; Gene; 1988; pp. 287-300; vol. 69.

Lakowicz, J. R. and Gryczynski, I.; Multiphoton Excitation of Biochemical Fluorophores; Topics in Fluorescence Spectroscopy: Nonlinear and Two-Photon-Induced Fluorescence 1997; pp. 87-144; vol. 5; ed. J. Lakowicz, Plenum Press, New York.

Holland, W. R. and Hall, D G.; Waveguide mode enhancement of molecular fluorescence; Optics Letters; 1985, pp. 414-416; vol. 10, No. 8.

Barnes, W. L.; Topical review: Fluorescence near interfaces: the role of photonic mode density; Journal of Modern Optics; 1998; pp. 661-669; vol. 45, No. 4.

Pettinger, B. and Gerolymatou, A.; Dyes Adsorbed at Ag-Colloids: Substitution of Fluorescence by Similarly Efficient Surface Fluorescence and Surface Raman Scattering; Ber. Bunsenges. Phys. Chem.; 1984; pp. 359-363; vol. 88; Verlag Chemie GmbH, D-6940 Weinheim.

Lobmaier, CH. et al.; Direct monitoring of molecular recognition processes using fluorescence enhancement at colloid-coated microplates; Journal of Molecular Recognition; 2001; pp. 215-222; vol. 14; John Wiley & Sons, Ltd.

Gersten, J. L. and Nitzan, A.; Photophysics and Photochemistry Near Surfaces and Small Particles; Surface Science; 1985; pp. 165-189; vol. 158; North-Holland, Amsterdam.

Drexhage, K. H.; Interaction of Light with Monomolecular Dye Layers; Progress in Optics, (Wolfe, E., Ed.); 1974; pp. 163-232; North Holland Publishing Company, Amsterdam.

Pasteur, L. et al.; Compte rendu sommaire des experiences faites a Pouilly-le-Fort, pres Melun, sur la vaccination charbonneuse; Comptes Rendus des seances De L'Academie des Sciences; 1881; pp. 1378-1383; vol. 92.

Stopa, P. J.; The Flow Cytometry of *Bacillus anthracis* Spores Revisited; Cytometry; 2000; pp. 237-244; vol. 41; published by Wiley-Liss, Inc.

Kreibig, U. et al.; Mie Resonances: Sensors for Physical and Chemical Cluster Interface Properties; Ber. Bunsenges. Phys. Chem.; 1997; pp. 1593-1604; vol. 101, No. 11; Wiley-VCH Verlag GmbH, D-69451 Weinheim.

Jeanmaire, D. L. and Van Duyne, R. P.; Surface Raman Spectroelectrochemistry, Part 1. Heterocyclic, Aromatic, and Aliphatic Amines Adsorbed on the Anodized Silver Electrode; J. Electroanal. Chem.; 1977; pp. 1-20; vol. 84; Printed in the Netherlands.

Sabanayagam, C. R. et al.; Oligonucleotide immobilization on micropatterned streptavidin surfaces; Nucleic Acids Research; 2000; p. e33; vol. 28, No. 8.

Shangkuan, Y.-H. et al.; Molecular characterization of *Bacillus anthracis* using multiplex PCR, ERIC-PCR and RAPD; Letters in Applied Microbiology; 2001; pp. 139-145; vol. 32.

Lee, M. A. et al.; Fluorescent detection techniques for real-time multiplex strand specific detection of *Bacillus anthracis* using rapid PCR; Journal of Applied Microbiology; 1999; pp. 218-223; vol. 87.

Berdal, B. P. et al.; Field Detection of *Francisella tularensis*; Scand. J. Infect. Dis.; 2000; pp. 287-291; vol. 32.

Leroy, E. M. et al.; Diagnosis of Ebola Haemorrhagic Fever by RT-PCR in an Epidemic Setting; Journal of Medical Virology; 2000; pp. 463-467; vol. 60.

Makino, S.-I. et al.; Detection of anthrax spores from the air by real-time PCR; Letters in Applied Microbiology; 2001; pp. 237-240; vol. 33.

Belgrader, P. et al.; A Battery-Powered Notebook Thermal Cycler for Rapid Multiplex Real-Time PCR Analysis; Analytical Chemistry; 2001; pp. 286-289; vol. 73, No. 2.

Aroca, R. et al.; Surface-Enhanced Raman Scattering of Langmuir-Blodgett Monolayers of Phthalocyanine by Indium and Silver Island Films; J. Phys. Chem.; 1985; pp. 4051-4054; vol. 89.

Sokolov, K. et al.: Enhancement of Molecular Fluorescence near the Surface of Colloidal Metal Films; Analytical Chemistry; 1998; pp. 3898-3905; vol. 70, No. 18.

Selvan, S. T. et al.; Remarkable Influence of Silver Islands on the Enhancement of Fluorescene from Eu3+ Ion-Doped Silica Gels; J. Phys. Chem. B; 1999; pp. 7064-7067; vol. 103.

Lakowicz, J. R.; Review: Radiative Decay Engineering: Biophysical and Biomedical Applications; Analytical Biochemistry; 2001; pp. 1-24; vol. 298.

Lacowicz, J. R. et al.; Radiative Decay Engineering: 2. Effects of Silver Island Films on Fluorescence Intensity, Lifetimes, and Resonance Energy Transfer; Analytical Biochemistry; 2002; pp. 261-277; vol. 301.

Zilinskas, R. A.; Iraq's Biological Weapons: The Past as Future?; JAMA; Aug. 1997; pp. 418-424; vol. 278(5).

Turnbull, P. C. B.; Definitive identification of *Bacillus anthracis*—a review; Journal of Applied Microbiology; 1999; pp. 237-240; vol. 87.

Keim, P. et al.; Molecular Evoluation and Diversity in *Bacillus anthracis* as Detected by Amplified Fragment Length Polymorphism Markers; Journal of Bacteriology; Feb. 1997; pp. 818-824; vol. 179, No. 3.

Keim; P. et al.; Multiple-Locus Variable-Number Tandem Repeat Analysis Reveals Genetic Relationships within *Bacillus anthracis*; Journal of Bacteriology; May 2000; pp. 2928-2936; vol. 182, No. 10.

Kunst, F.; The complete genome sequence of the Gram-positive bacterium *Bacillus subtilis*; Nature; Nov. 1997; pp. 249-256; vol. 390.

Helgason, E. et al.; *Bacillus anthracis, Bacillus cereus,* and *Bacillus thuringiensis*—One Species on the Basis of Genetic Evidence; Applied and Environmental Microbiology; Jun. 2000; pp. 2627-2630; vol. 66, No. 6.

Takami, H. et al.; Complete genome sequence of the alkaliphilic bacterium *Bacillus halodurans* and genomic comparison with *Bacillus subtilis*; Nucleic Acids Research; 2000; pp. 4317-4331; vol. 28, No. 21.

Aronson, A.; Sporulation and delta-endotoxin synthesis by *Bacillus thuringiensis*; Cell. Mol. Life Sci.; 2002; pp. 417-425; vol. 59.

Okinaka, R. T. et al.; Sequence and Organization of pX01, the Large *Bacillus anthracis* Plasmid Harboring the Anthrax Toxin Genes; Journal of Bacteriology; Oct. 1999; pp. 6509-6515; vol. 181; No. 20.

Okinaka, R. et al.; Sequence, assembly and analysis of pX01 and pX02; Journal of Applied Microbiology; 1999; pp. 261-262; vol. 87.

Ramisse, V. et al.; The Ba813 chromosomal DNA sequence effectively traces the whole *Bacillus anthracis* community; Journal of Applied Microbiology; 1999; pp. 224-228; vol. 87.

Michaels, A. M. et al.; Ag Nanocrystal Junctions as the Site for Surface-Enhanced Raman Scattering of Single Rhodamine 6G Molecules; J. Phys. Chem. B; 2000; pp. 11965-11971; vol. 104.

Freeman, R. G. et al.; Self-Assembled Metal Colloid Monolayers: An Approach to SERS Substrates; Science, New Series (JSTOR); Mar. 1995; pp. 1629-1632; vol. 267, No. 5204.

Ambrose, W. P. et al.; Single Molecule Fluorescence Spectroscopy at Ambient Temperature; Chem. Rev.; 1999; pp. 2929-2956; vol. 99; USA.

Bohme, P. et al.; Self-Assembled Monolayers on Polymer Surfaces: Kinetics, Functionalization, and Photopatterning; Langmuir; 1999; pp. 5323-5328; vol. 15.

Rivas, L. et al.; Growth of Silver Colloidal Particles Obtained by Citrate Reduction to Increase the Raman Enhancement Factor; Langmuir; 2001; pp. 574-577; vol. 17.

Bright, R. M. et al.; Preparation and Characterization of Ag Colloid Monolayers; Langmuir; 1998; pp. 5695-5701; vol. 14.

Ni, F. and Cotton, T. M.; Chemical Procedure for Preparing Surface-Enhanced Raman Scattering Active Silver Films; Analytical Chemistry; 1986; pp. 3159-3163; vol. 58; USA.

Link, S. and El-Sayed, M. A.; Spectral Properties and Relaxation Dynamics of Surface Plasmon Electronic Oscillations in Gold and Silver Nanodots and Nanorods; J. Phys. Chem. B; 1999; pp. 8410-8426; vol. 103; USA.

Caruso, F. et al.; Nanoengineering of Inorganic and Hybrid Hollow Spheres by Colloidal Templating; Science; Nov. 1998; pp. 1111-1114; vol. 282 (5391).

Yee, J. K. et al.; Modification of Quartz Surfaces via Thiol-Disulfide Interchange; Langmuir; 1991; pp. 307-313; vol. 7.

Lenigk, R. et al.; Surface Characterization of a Silicon-Chip-Based DNA Microarray; Langmuir; 2001; pp. 2497-2501; vol. 17.

Okamoto, T. et al.; Microarray fabrication with covalent attachment of DNA using Bubble Jet technology; Nature Biotechnology; Apr. 2000; pp. 438-441; vol. 18.

Mandal, S. et al.; Studies on the Reversible Aggregation of Cysteine-Capped Colloidal Silver Particles Interconnected via Hydrogen Bonds; Langmuir; 2001; pp. 6262-6268; vol. 17.

Lazarides, A. A. and Schatz, G. C.; DNA-Linked Metal Nanosphere Materials: Structural Basis for the Optical Properties; J. Phys. Chem. B; 2000; pp. 460-467; vol. 104; USA.

Graham, D. et al.; Selective Detection of Deoxyribonucleic Acid at Ultralow Concentrations by SERRS; Analytical Chemistry; 1997; pp. 4703-4707; vol. 69.

Sun, Y.-P. et al.; Strong Optical Limiting of Silver-Containing Nanocrystalline Particles in Stable Suspensions; J. Phys. Chem. B; 1999; pp. 77-82; vol. 103.

Geddes; C. D. et al.; 1- and 2-Photon Fluorescence Anisotropy Decay in Silicon Alkoxide Sol-Gels: Interpretation in Terms of Self-assembled Nanoparticles; J. Phys. Chem. B; 2002; pp. 3835-3841; vol. 106.

Esumi, K. et al.; Role of Poly(amidoamine) Dendrimers for Preparing Nanoparticles of Gold, Platinum, and Silver; Langmuir; 2000; pp. 2604-2608; vol. 16.

Foldes-Papp, Z. et al.; Fluorescent high-density labeling of DNA: error-free substitution for a normal nucleotide; Journal of Biotechnology; 2001; pp. 237-253; vol. 86.

Gryczynski, I. et al.; The CFS Engineers the Intrinsic Radiative Decay Rate of Low Quantum Yield Fluorophores; Journal of Fluorescence; Mar. 2002; pp. 11-13; vol. 12, No. 1.

Diaspro, A.; Introduction to Two-Photon Microscopy; Microscopy Research and Technique; 1999; pp. 163-164; vol. 47.

Graham, D. et al.; Surface-Enhanced Resonance Raman Scattering as a Novel Method of DNA Discrimination; Angew. Chem. Int. Ed.; 2000; pp. 1061-1063; vol. 39, No. 6.

Comor, M. I. and Nedeljkovic, J. M.; Enhanced photocorrosion stability of colloidal cadmium sulphide-silica nanocomposites; Journal of Materials Science Letters; 1999; pp. 1583-1585; vol. 18.

Toshima, N. And Yonezawa, T.; Bimetallic nanoparticles—novel materials for chemical and physical applications; New J. Chem.; 1998; pp. 1179-1201.

Pastoriza-Santos, I. et al.; Self-Assembly of Silver Particle Monolayers on Glass from Ag+ Solutions in DMF; Journal of Colloid and Interface Science; 2000; pp. 236-241; vol. 221.

De Saja-Gonzalez, J. et al.; Spectroscopic characterization and Langmuir-Blodgett films of N,N'-bis(3-aminophenyl)-3,4:9,10-perylenebis(dicarboximide); Materials Science and Engineering C 5; 1998; pp. 297-299.

De Saja-Gonzalez, J. et al.; Surface-enhanced fluorescence and SERRS spectra of N-octadecyl-3,4:9,10-perylenetetracarboxylic monoanhydride on silver island films; Spectrochimica Acta Part A; 1997; pp. 173-181; vol. 53.

Constantino, C. J. L. and Aroca, R. F.; Surface-enhanced resonance Raman scattering imaging of Langmuir-Blodgett monolayers of bis(benzimidazo)perylene on silver island films; Journal of Raman Spectroscopy; 2000; pp. 887-890; vol. 31.

Constantino, C. J. L. et al.; Surface enhanced fluorescence and Raman imaging of Langmuir-Blodgett azopolymer films; Spectrochimica Acta Part A; 2001; pp. 281-289; vol. 57.

Garoff, S. et al.; Electrodynamics at rough metal surfaces: Photochemistry and luminescence of adsorbates near metal-island films; J. Chem. Phys.; Dec. 1984; pp. 5189-5200; vol. 81(11).

Link, S. and El-Sayed, M. A.; Shape and size dependence of radiative, non-radiative and photothermal properties of gold nanocrystals; Int. Reviews in Physical Chemistry; 2000; pp. 409-453; vol. 19, No. 3.

Chen, C. J. and Osgood, R. M.; Direct Observation of the Local-Field-Enhanced Surface Photochemical Reactions; Physical Review Letters; May 1983; pp. 1705-1708; vol. 50, No. 1. USA.

Amos, R. M. and Barnes, W. L.; Modification of spontaneous emission lifetimes in the presence of corrugated metallic surfaces; Physical Review B; Mar. 1999; pp. 7708-7714; vol. 59, No. 11; USA.

Huang, Z. et al.; Spontaneous Lifetime and Quantum Efficiency in Light Emitting Diodes Affected by a Close Metal Mirror; IEEE Journal of Quantum Electronics; Dec. 1993; pp. 2940-2949; vol. 29, No. 12.

Amos, R. M. and Barnes, W. L.; Modification of the spontaneous emission rate of Eu3+ ions close to a thin metal mirror; Physical Review B; Mar. 1997; pp. 7249-7254; vol. 55, No. 11. USA.

Little, S. F. and Ivins, B. E.; Molecular pathogenesis of *Bacillus anthracis* infection; Microbes and Infection; 1999; pp. 131-139; vol. 2.
Strickler, S. J. and Berg, R. A.; Relationship between Absorption Intensity and Fluorescence Lifetime of Molecules; The Journal of Chemical Physics; Aug. 1962; pp. 814-822; vol. 37, No. 4.
Geddes, C. D. and Lakowicz, J. R.; Metal-Enhanced Fluorescence; Journal of Fluorescence; Jun. 2002; pp. 121-129; vol. 12, No. 2.
Benner, R. E. et al.; Angular Emission Profiles of Dye Molecules Excited by Surface Plasmon Waves at a Metal Surface; Optics Communications; Aug. 1979; pp. 145-149; vol. 30, No. 2.
Campion, A. et al.; Electronic Energy Transfer to Metal Surfaces: A Test of Classical Image Dipole Theory at Short Distances; Chemical Physics Letters; Aug. 1980; pp. 447-450; vol. 73, No. 3.

Fleischmann, M. et al.; Raman Spectra of Pyridine Adsorbed at a Silver Electrode; Chemical Physics Letters; May 1974; pp. 163-166; vol. 26, No. 2.

Wokaun, A. et al.; Energy transfer in surface enhanced luminescence; J. Chem. Phys.; Jul. 1983; pp. 509-514; vol. 79(1); USA.

Vo-Dinh, T.; Surface-enhanced Raman spectroscopy using metallic nanostructures; Trends in Analytical Chemistry; 1998; pp. 557-582; vol. 17, Nos. 8+9.

Shirtcliffe, N. et al.; Reproducible Preparation of Silver Sols with Small Particle Size Using Borohydride Reduction: for Use as Nuclei for Preparation of Larger Particles; Journal of Colloid and Interface Science; 1999; pp. 122-129; vol. 211.

Fox et al. 2002. Report of the Bioterrorism Workshop. J. Microbial Methods, 51: 247-254.

Virtanen, M. et al. 1983. Novel Test for Rapid Viral Diagnosis: Detection of Adenovirus in Nasopharyngeal Mucus Aspirates by Means of Nucleic-Acid Sandwich Hybridisation. The Lancet, 1(8321): 381-383.

* cited by examiner

HIGH-SENSITIVITY ASSAYS FOR PATHOGEN DETECTION USING METAL ENHANCED FLUORESCENCE

CROSS-REFERENCE TO RELATED APPLICATIONS

This application is filed under the provisions of 35 U.S.C. §371 and claims the priority of International Patent Application No. PCT/US2003/038163 on Nov. 26, 2003, which in turn claims priority of U.S. Provisional Patent Application No. 60/429,263 filed on Nov. 26, 2002.

BACKGROUND OF THE INVENTION

1. Field of Invention

The present invention relates generally to methods and systems for detecting a pathogen, and more particularly, to methods and systems using metal-enhanced fluorescence due to interactions of fluorophores with metallic particles and/or surfaces.

2. Description of the Related Art

The 2001 terror attacks in the United States clearly demonstrated a need for rapid detection systems for unequivocal identification of bio-warfare/bio-terrorism agents such as *Bacillus Anthracis*, the causative agent of anthrax. The ability to accurately identify biological threat agents in real time will enable first responders and clinicians to make informed decisions about the most appropriate countermeasures.

*Bacillus anthracis*, the virulent, endospore-forming bacterium notorious for its recent use as a bioterror weapon, has plagued humans and livestock for many years [34]. The bacterium was intimately associated with the founding of the sciences of bacteriology and immunology, highlighted by Pasteur's famous demonstration of vaccine protection of sheep at Pouilly-le-Fort, France in 1881 [35]. Since then, little attention has been focused on understanding the biology of the organism, save for the fact that it possesses properties that make it ideally suited as a biological weapon. It forms heat resistant spores that are easy to produce using commercially available technology and can infect via the aerosol route. It has been reported that at the time of the Gulf War, Iraq produced large quantities of anthrax spores and had deployed SCUD/Al-Hussein missiles equipped with biological weapons warheads [36].

*Bacillus anthracis* is the only obligate pathogen within the genus *Bacillus*, which comprises the Gram-positive aerobic or facultatively anaerobic spore-forming, rod-shaped bacteria. It is frequently convenient to class *B. anthracis* informally within the *B. cereus* group, which, on the basis of phenotype, comprises *B. cereus, B. anthracis, B. thuringiensis* and *B. mycoides* [37]. It is not possible to discriminate between species in this group based on 16S rRNA sequences. However, amplified fragment length polymorphism (AFLP) and multiple-locus VNTR (variable number tandem repeat) analysis (MLVA analysis) have provided clear evidence that *B. anthracis* can be distinguished reliably from other members of the bacilli [38,39]. In practical terms, the demonstration of virulence constitutes the principle point of difference between typical strains of *B. anthracis* and those of other anthrax-like organisms [40].

While *Bacillus anthracis* can kill a broad range of animals, other members of the Gram-positive *Bacillus* genus are typically soil-dwellers that cause, at worst, mild opportunistic infections. *B. anthracis* is a member of the *B. cereus* group of very closely-related, ubiquitous, soil bacteria [41,42] phylogenetically separate from the other completely sequenced *Bacillus* genomes, *B. subtilis* [41] and *B. halodurans* [43]. The nature of the virulence of individual strains in the *B. cereus* group is often determined by genes carried on large plasmids. For instance, *B. thuringiensis* strains are distinguished by their production of plasmid-encoded insecticidal crystal toxins (δ-endotoxins) of different specificity [44]. For *B. anthracis*, genes for the anthrax toxin complex and poly-D-glutamic acid capsule are found on plasmid pX01 (181.6 kb) [45] and pX02 (96 kb) [46] respectively. While the plasmid genes are necessary for full virulence, the contributions of chromosomal determinants to the complex pathogenesis of anthrax are still largely unknown.

The US anthrax bio-terrorism attack in the autumn of 2001 offered a tragic "proof of principle" of the danger of *B. anthracis* and has spurred numerous efforts by the biomedical community to improve forensics and medical countermeasures against the bacterium. In the key area of agent detection and warning, major advances have been made. For example, systems capable of detecting aerosolized agents have been developed and deployed based on DNA (BASIS) and antibody based technologies (Portal Shield). The ground breaking work of Department of Energy (DOE) researchers looking at aerosol samples from 11 major US cities found that nonpathogenic, close relatives of *B. anthracis* could be detected year round and that their abundance varied with the season [47]. However, experience gained from the field has shown that differentiating threat agents, particularly *B. anthracis* from other nonpathogenic dose relatives is challenging.

When compared to other bacterial genomes, most *B. anthracis* proteins have their highest level of similarity to other *Bacillus* genomes (*B. subtilis* (2065 (36%)) and *B. halodurans* (1082 (19%)). Most *B. anthracis* chromosomal proteins have homologs in the draft sequence of the *B. cereus* 10987 genome, confirming the very close relationship between these organisms. There are 642 genes in *B. anthracis* without matches in *B. subtilis, B. halodurans* or *B. cereus* 10987, but these are mostly small hypothetical proteins. Only 43 have a predicted function and these numbers may be lower when the completed *B. cereus* 10987 genome is available. These genes may define unique phenotypic characteristics of *B. anthracis*, which could be potentially of great interest in regard to virulence.

Traditional laboratory based methods have exploited these differences but can take several days to produce results. In the context of a biological attack this is an unacceptable delay if resulting casualties are to be minimized. The need for "real-time" (<60 mins) detection has lead to the development of technologies based on DNA (PCR) and protein (antibody) targets [37]. PCR and reverse transcriptase PCR assays have been reported for detecting anthrax [1,2] in air samples [5], anthrax spore detection by flow cytometry [6], microsonication to disrupt bacterial spores [7] and real-time devices for PCR analysis [8].

However, these advances are not considered simple or monetarily reasonable, and therefore limit their potential as field-deployable, emerging technologies for use in ultra-sensitive pathogen detection.

Other methods include use of a detection label such as a linked fluorescent dye molecule, such as fluorescein isothiocyanate, rhodamine, Cascade blue, that absorb electromagnetic energy in a particular absorption wavelength spectrum and subsequently emit visible light at one or more longer (i.e., less energetic) wavelengths. The fluorescent molecules (fluorophores) can be detected by illumination with light of an appropriate excitation frequency and the resultant spectral emissions can be detected by electro-optical sensors or light microscopy. A wide variety of fluorescent dyes are available and offer a selection of excitation and emission spectra. Unfortunately, detection methods that employ fluorescent labels are of limited sensitivity for a variety of reasons. Firstly, the lifetime of the fluorescence emission is usually short, on the order of 1 to 100 ns. Further, the limit of detection of from typical fluorophores is limited by the significant background noise contributed by nonspecific fluorescence and reflected excitation light. Additionally, organic dye fluorophores are susceptible to photolytic decomposition of the dye molecule (i.e., photobleaching). Thus, even in situations where background noise is relatively low, it is often not possible to integrate a weak fluorescent signal over a long detection time, since the dye molecules decompose as a function of incident irradiation in the UV and near-UV bands.

Thus, there is a need for a detection method and system using fluorophores that identifies the pathogenic agent and preferably able to differentiate between multiple agents, that does not suffer from the problems of the prior art and does not require any amplification steps, such as in PCR or ELISA.

SUMMARY OF THE INVENTION

In one aspect, the present invention relate to a DNA sequence based micro-assay approach with metallic-fluorophore combinations to provide superior high sensitivity detection, low copy number detection and single copy-number detection.

In another aspect, the present invention relates to a method for detecting the class A agent anthrax using a single-copy number detection method without the need for any amplification steps that can also be applied to the detection of plague, smallpox, tularemia, botulism (botulinum toxin) or any other organism where the DNA sequence is known.

In yet another aspect, the present invention relates to a method for detecting a pathogen in a sample, the method comprising:

a) providing a system comprising:
   - a layer of immobilized metal particles positioned on a surface substrate, wherein the immobilized metal particles have attached thereto a captured biomolecular probe with an affinity for the target pathogen; and
   - a free biomolecular probe with an affinity for the target pathogen, wherein the free biomolecular probe has attached thereto a fluorophore;

b) contacting the sample with the immobilized biomolecular probes, wherein the target pathogen binds to the immobilized biomolecular probes; and c) contacting the bound target pathogen with the free biomolecular probe, wherein binding of the free biomolecular probe to the target pathogen causes the fluorophore to be positioned a sufficient distance from the immobilized metal particles to enhance fluorescence emission when excited by an irradiating source.

In a further aspect, the present invention provides a method for detecting a pathogen in a sample, the method comprising:

a) providing a system comprising:
   - a immobilized metallized surface positioned on a surface substrate, wherein the immobilized metallized surface has attached thereto an immobilized capture DNA sequence probe complementary to a known DNA sequence of the target pathogen; and
   - a free capture DNA sequence probe complementary to a known DNA sequence of the target pathogen, wherein the free capture DNA sequence probe has attached thereto a fluorophore;

b) contacting the sample with the immobilized capture DNA sequence probe, wherein the DNA sequence of the target pathogen binds to the immobilized capture DNA sequence probe;

c) contacting the bound DNA sequence of the target pathogen with the free capture DNA sequence probe, wherein binding of the free capture DNA sequence probe to the DNA sequence of the target pathogen causes the fluorophore to be positioned a sufficient distance from the immobilized metallized surface to enhance fluorescence emission when excited by an irradiating source; and d) identifying the target pathogen by fluorescence emission by irradiating the system with an irradiating source to excite the fluorophore.

In still a further aspect, the above-described method further comprises a metal colloid attached to the free capture DNA sequence probe and positioned for sandwiching the fluorophore between the metal colloid and immobilized metal particles on the surface substrate.

Another aspect of the present invention relates to an assay system comprising:

- a layer of immobilized metal particles deposited on a surface substrate, wherein a captured DNA probe complementary to a known DNA sequence of the target pathogen is immobilized on the metal particles;
- a free DNA probe complementary to the known DNA of the target pathogen, wherein the free DNA probe has attached thereto a fluorophore; wherein binding of the immobilized and free DNA probe to the target pathogen causes the fluorophore to be positioned a sufficient distance from the immobilized metal particles to enhance fluorescence emission.

Yet another aspect relates to an assay system for detecting a target pathogen comprising:

- a layer of immobilized metal particles deposited on a surface substrate, wherein a captured biomolecular probe having an affinity for a target pathogen is immobilized on the metal particles;
- a free biomolecular probe having an affinity for a target pathogen, wherein the free biomolecular probe has attached thereto a fluorophore; wherein binding of the immobilized and free biomolecular probe to the target pathogen causes the fluorophore to be positioned a sufficient distance from the immobilized metal particles to enhance fluorescence emission when excited by an irradiating source.

The present invention further comprises a detection device for detecting fluorescence emissions including, but not limited to visual inspection, digital (CCD) cameras, video cameras, photographic film, or the use of current instrumentation such as laser scanning devices, fluorometers, luminometers, photodiodes, quantum counters, plate readers, epifluorescence microscopes, scanning microscopes, confocal microscopes, capillary electrophoresis detectors, or other light detector capable of detecting the presence, location, intensity, excitation and emission spectra, fluorescence polarization, fluorescence lifetime, and other physical properties of the fluorescent signal.

A further aspect of the present invention, relates to a kit for detecting a target pathogen in a sample, the kit comprising

- a container comprising a layer of immobilized metal particles deposited on a surface substrate, wherein a captured biomolecular probe is immobilized on the metal particles and wherein the captured biomolecular probe has an affinity for a target pathogen of interest; and
- a free biomolecular probe having an affinity for a target pathogen, wherein the free biomolecular probe has attached thereto a fluorophore and wherein binding of the target pathogen to both the immobilized and free biomolecular probe causes the fluorophore to be positioned a sufficient distance from the immobilized metal particles to enhance fluorescence emission, wherein the immobilized and free biomolecular probe can be in the same or different containers.

Other aspects and advantages of the invention will be more fully apparent from the ensuing disclosure and appended claims.

DETAILED DESCRIPTION OF THE PRESENT INVENTION

Figure 1:
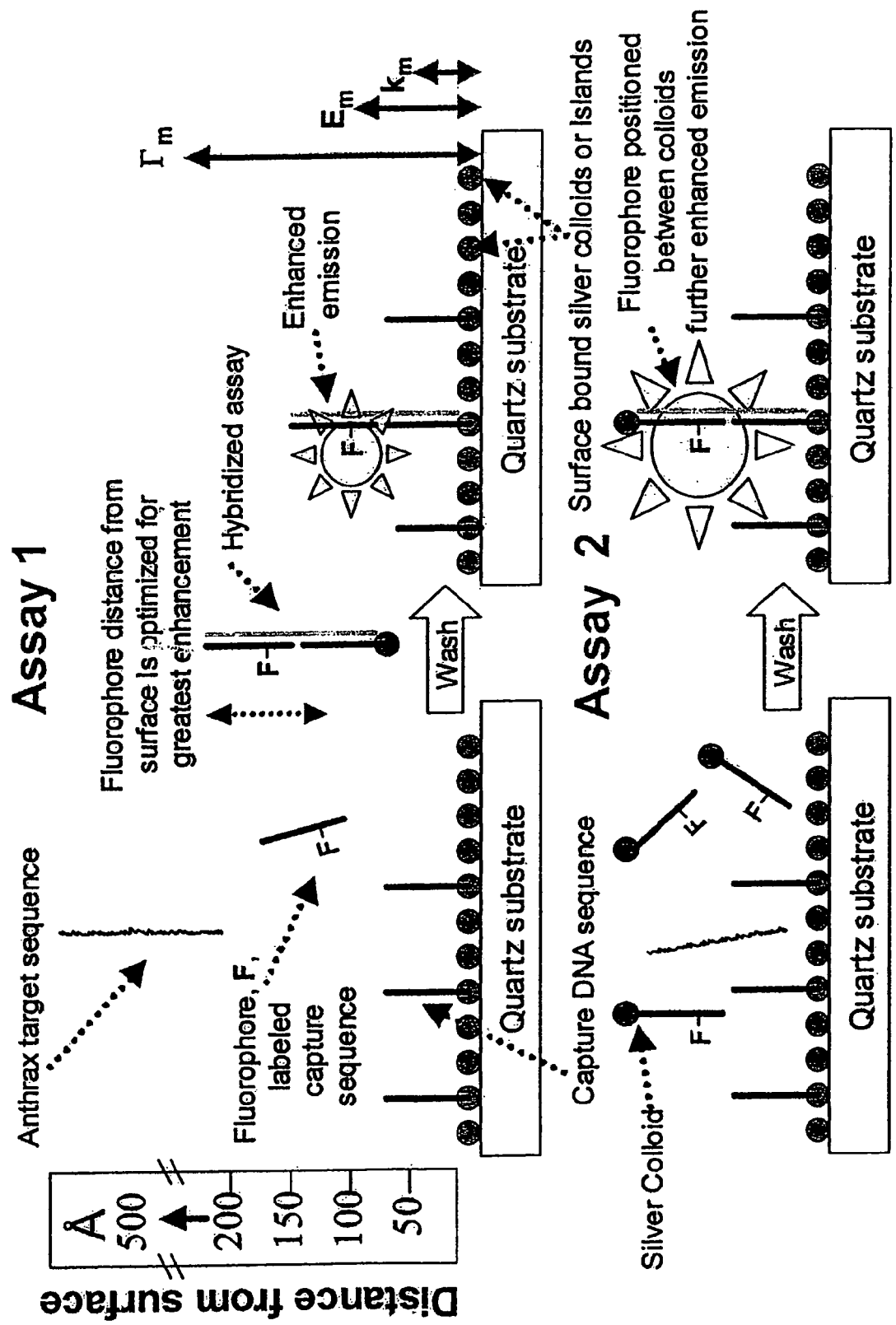
FIG. 1 illustrates two assays, Assay 1 shows a capture DNA sequence that is immobilized to a silver surface and Assay 2 shows the fluorophore labeled capture DNA sequence also has an attached silver colloid.

Before the present invention is disclosed and described, it is to be understood that this invention is not limited to the particular process steps and materials disclosed herein as such process steps and materials may vary somewhat. It is also to be understood that the terminology used herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural references unless the content clearly dictates otherwise.

As used hereinafter the terms fluorescent dye, fluorochrome, or fluorophore are used interchangeably and bear equivalent meanings. Fluorophore used in this invention are preferably of the general class known as cyanine dyes, with emission wavelengths between 550 nm and 900 nm. These dyes may contain methine groups and their number influences the spectral properties of the dye. The monomethine dyes that are pyridines typically have blue to blue-green fluorescence emission, while quinolines have green to yellow-green fluorescence emission. The trimethine dye analogs are substantially shifted toward red wavelengths, and the pentamethine dyes are shifted even further, often exhibiting infrared fluorescence emission.

In addition to fluorophores discussed above, related dyes can be further selected from cyclobutenedione derivatives, substituted cephalosporin compounds, fluorinated squaraine compositions, symmetrical and unsymmetrical squaraines, alkylalkoxy squaraines, or squarylium compounds. Some of these dyes can fluoresce at near infrared as well as at infrared wavelengths that would effectively expand the range of emission spectra up to about 1,000 nm. In addition to squaraines, i.e., derived from squaric acid, hydrophobic dyes such as phthalocyanines and naphthalocyanines can also be selected to operate at longer wavelengths. Other classes of fluorophores include 3-Hydroxypyrene 5,8,10-Tri Sulfonic acid, 5-Hydroxy Tryptamine, 5-Hydroxy Tryptamine (5-HT), Acid Fuhsin, Acridine Orange, Acridine Red, Acridine Yellow, Acriflavin, AFA (Acriflavin Feulgen SITSA), Alizarin Complexon, Alizarin Red, Allophycocyanin, ACMA, Aminoactinomycin D, Aminocoumarin, Anthroyl Stearate, Aryl- or Heteroaryl-substituted Polyolefin, Astrazon Brilliant Red 4 G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, BOBO 1, Blancophor FFG Solution, Blancophor SV, Bodipy F1, BOPRO 1, Brilliant Sulphoflavin FF, Calcien Blue, Calcium Green, Calcofluor RW Solution, Calcofluor White, Calcophor White ABT Solution, Calcophor White Standard Solution, Carbocyanine, Carbostyryl, Cascade Blue, Cascade Yellow, Catecholamine, Chinacrine, Coriphosphine O, Coumarin, Coumarin-Phalloidin, CY3.1 8, CY5.18, CY7, Dans (1-Dimethyl Amino Naphaline 5 Sulphonic Acid), Dansa (Diamino Naphtyl Sulphonic Acid), Dansyl NH-CH3, DAPI, Diamino Phenyl Oxydiazole (DAO), Dimethylamino-5-Sulphonic acid, Dipyrromethaneboron Difluoride, Diphenyl Brilliant Flavine 7GFF, Dopamine, Eosin, Erythrosin ITC, Ethidium Bromide, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Hoechst 33258, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nile Red, Nitrobenzoxadidole, Noradrenaline, Nuclear Fast Red, Nuclear Yellow, Nylosan Brilliant Flavin E8G, Oregon Green, Oxazine, Oxazole, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Propidium Iodide, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Rose Bengal, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Texas Red, Thiazine Red R, Thioflavin S, Thioflavin TCN, Thioflavin 5, Thiolyte, Thiozol Orange, Tinopol CBS, TOTO 1, TOTO 3, True Blue, Ultralite, Uranine B, Uvitex SFC, Xylene Orange, XRITC, YO PRO 1, or combinations thereof.

One skilled in the art would know which one to select among such fluorescence dyes as long as the desired emission and absorption properties as well as their hydrophobic properties are appropriate. The spectral properties of the fluorescent dyes should be sufficiently similar in excitation wavelengths and intensity to fluorescein or rhodamine derivatives as to permit the use of the same.

Attaching of the fluorophore to the immobilized and/or free biomolecular probe may be achieved by any of the techniques familiar to those skilled in the art. For example, the fluorophore may be covalently attached to the bimolecular probe by methods disclosed in U.S. Pat. No. 5,194,300 Cheung and U.S. Pat. No.4,774,189 Schwartz.

In another embodiment, the assay system of the present invention provides for detecting and separating at least two target pathogen by choosing fluorophores such that they possess substantially different emission spectra, preferably having emission maxima separated by greater than 10 nm, more preferably having emission maxima separated by greater than 25 nm, even more preferably separated by greater than 50 nm. When differentiation between the two fluorophores is accomplished by visual inspection, the two dyes preferably have emission wavelengths of perceptibly different colors to enhance visual discrimination. When it is desirable to differentiate between the two fluorophores using instrumental methods, a variety of filters and diffraction gratings allow the respective emission maxima to be independently detected.

The technology used in the disclosed assay is "Metal-Enhanced Fluorescence" (MEF), or in the alternative Surface-Enhanced Fluorescence (SEF), whereby metallic particles can interact with fluorophores (by modifying their free-space conditions), producing ultra-bright fluorophores, which are both more photostable and can emit approximately $10^6$ more photons per fluorophore before photodestruction.

MEF is enhanced by further exploiting another complimentary property of the metal-fluorophore combinations, namely the "enhanced rate of excitation" ($E_m$), where a red-pulsed laser diode and light emitting diode can serve as sources for two-photon excitation of labeled fluorophores. Such excitation sources and assay also provide an inexpensive field-deployable anthrax detection system. Up to about $10^{10}$ fold enhancement in the fluorescence signal may be obtained when using two-photon excitation, allowing the detection of single copies of anthrax DNA.

Two assays are disclosed in FIG. 1. Assay 1 comprises a capture DNA sequence that is immobilized to a silver surface (immobilized colloids or islands). Target DNA hybridizes to this capture DNA sequence and to a fluorophore labeled capture sequence. The bound target DNA is detected by the enhanced fluorescence from the bound fluorophore labeled capture sequence. Both capture DNA sequences (one surface-bound and one free in solution) are designed and fabricated in such a way that they are complimentary to a known target pathogen DNA sequence (or any DNA sequence, depending upon the assay). When the two capture sequences bind the target DNA strand, the fluorophore located on the free capture strand is positioned within the enhancing region, from about 50 Å to about 500 Å from the silver surface. Only by the binding of a complimentary anthrax DNA target strand will any fluorescence be observed, as a low quantum yield fluorophore is used. This provides a desirable low fluorescence background for the assay. Using 2-photon excitation to spatially localize the excitation to only fluorophores that are in close proximity to the silver surface (50-500 Å), the fluorescence signal level is substantially increased, as is the assay signal-to-noise ratio.

In Assay 2, the fluorophore labeled capture DNA sequence also has an attached silver colloid. The fluorescence signal in this assay is further enhanced by the presence of silver colloids above and below the fluorophore upon hybridization to the target DNÁ sequence.

It is important to include a stable, non-transferable chromosomal target [49] for the target pathogen DNA sequence and importantly, the chromosomal gene targets must be usable to discriminate *B. anthracis* and other members of the *B. cereus* group [37,50].

Knowledge about fluorescence is based on measurements of the spectroscopic properties of fluorophores that upon excitation, radiate into a homogeneous and non-conducting medium, typically referred to as free space. These spectral properties are well described by Maxwell's equations for a radiating oscillating dipole. However, the interactions of an emitting dipole with physical objects can be considerably more complex, as known from antenna and receiver design. The size and shape of an antenna are designed with the goal of directing the radiation and accounting for its interactions with the earth's surface. A fluorophore is also like an antenna, but one which oscillates at high frequency and radiates short wavelengths. Local effects are not usually seen because of the small size of fluorophores relative to the experimental apparatus.

In most spectroscopic measurements, the solutions or medium is transparent to the emitted and sampling radiation. However there are several important exceptions to the free space condition. One well-known example is Surface Enhanced Raman Scattering (SERS) [9-14]. It is known that the presence of a metallic surface can enhance the Raman signals by factors of $10^3$ to $10^8$, and reports of even larger enhancements have appeared. The presence of a nearby metal film, island or particle can also alter the emission properties of fluorophores. The most well known effect is the quenching of fluorescence by a near-by metal. The emission of fluorophores within 50 Å of a metal surface is almost completely quenched. This effect is used in fluorescence microscopy with evanescent wave excitation. For a fluorophore located on a cell membrane and near the quartz-water interface the fluorescence emission is quenched, allowing selective observation of the emission from a fluorophore in the cytoplasmic region of the cell which is more distant from the solid-liquid interface [15]. In addition to quenching, metal surfaces or particles can cause significant increases in fluorescence. Remarkably, depending on the distance and geometry, metal surfaces or particles can result in enhancement factors of up to 1000 for the fluorescence emission [16-18]. Fluorophores near a metal film are not expected to emit isotropically, but rather the emission is directed into selected directions which are dependent on the sample configuration and the nature of the metallic surface [19-24]. In addition to directionality, the decay times of fluorophores are altered by the metal. In fact the lifetimes of fluorophores placed at fixed distances from a continuous metallic-surface oscillate with distance [21].

Figure 2:
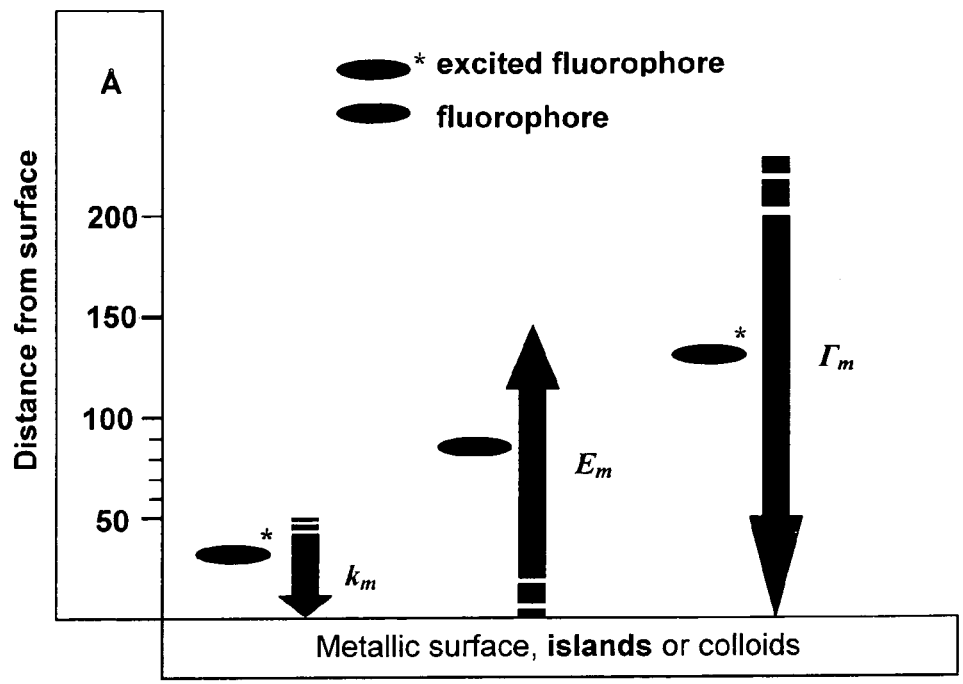
FIG. 2 illustrates the effects of local metallic colloids on a nearby fluorophore

The effects of metallic particles and surfaces on fluorophores are due to at least three known mechanisms as described in FIG. 2. One mechanism is energy transfer quenching, $k_m$, to the metals with a $d^{-3}$ dependence [22]. This quenching can be understood by damping of the dipole oscillations by the nearby metal. A second mechanism is an increase in the emission intensity due to the metal increasing the local incident field on the fluorophore, $E_m$, with a maximum theoretical enhancement effect of about 140. This effect has been observed for metal colloids and is appropriately called the "Lightning Rod effect" [23-25]. This enhancement can be understood as due to the metal particles on concentrating the local field and subsequently increasing the rate of excitation. The third mechanism is that a nearby metal can increase the intrinsic decay rate of the fluorophore, $\Gamma_m$, that is, to modify the rate at which the fluorophore emits photons [26-29]. These later two fluorophore-metal interactions offer remarkable opportunities for advanced fluorescence assay-technology [26,27,30].

The distance dependence of fluorescence enhancements and those of quenching may be determined by standard methods disclosed herein.

In fluorescence, the spectral observables are governed by the magnitude of $\Gamma$, the radiative rate, relative to the sum of the non-radiative decay rates, $k_{nr}$, such as internal conversion and quenching. In the absence of metallic particles or surfaces, the quantum yield, $Q_0$ and fluorescence lifetime $\tau_0$ are given by:

$$Q_0 = \frac{\Gamma}{\Gamma + k_{nr}}$$

$$\tau_0 = \frac{1}{\Gamma + k_{nr}}$$

Fluorophores with high radiative rates have high quantum yields and short lifetimes Increasing the quantum yield requires decreasing the non-radiative rates $k_{nr}$, which is often only accomplished when using low solution temperatures or a fluorophore binding in a more rigid environment. The natural lifetime of a fluorophore, $\tau_N$, is the inverse of the radiative decay rate or the lifetime, which would be observed if the quantum yield were unity. This value is determined by the oscillator strength (extinction coefficient) of the electronic transition [31]. The extinction coefficients of chromophores are only very slightly dependent on their environment. Hence for almost all examples currently employed in fluorescence spectroscopy, the radiative decay rate is essentially constant.

Figure 3:
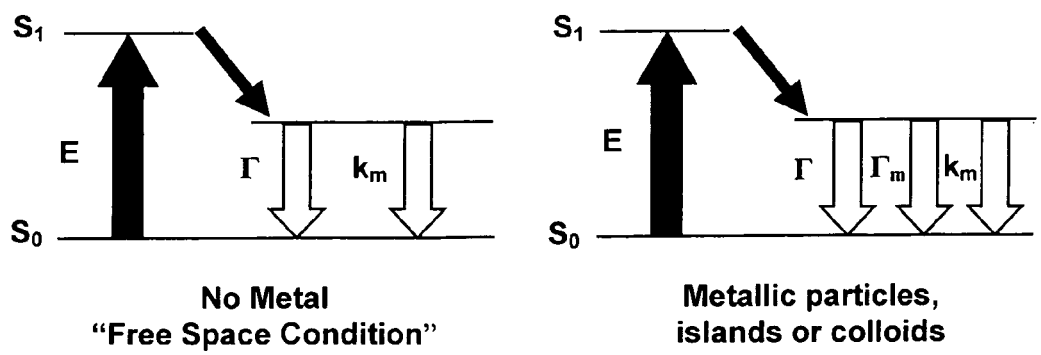
FIG. 3 illustrates a classical Jablonski diagram for the free space condition and the modified form in the presence of metallic particles, islands or colloids. E=excitation, $\Gamma_m$=radiative rate in the presence of metal

The concept of modifying the radiative decay rate of fluorophores is unfamiliar to most spectroscopists. It is therefore intuitive to consider the novel effects of fluorescence enhancement due to metal particles, m, by assuming an additional radiative rate, $\Gamma_m$, as shown in FIG. 3. In this case the quantum yield and lifetime are given by:

$$Q_m = \frac{\Gamma + \Gamma_m}{\Gamma + \Gamma_m + k_{nr}}$$

$$\tau_m = \frac{1}{\Gamma + \Gamma_m + k_{nr}}$$

Figure 4:
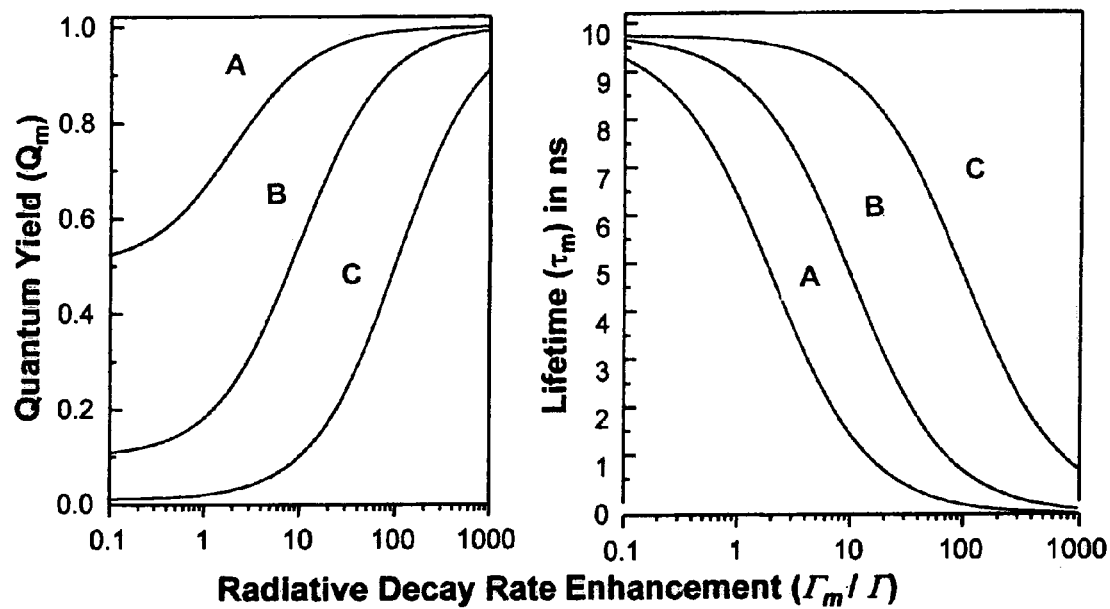
FIG. 4 illustrates metal-induced effects on the fluorescence quantum yield (left) and lifetime (right). Three simulation for quantum yield of 0.5 (A), 0.10 (B), and 0.01 (C) have been assumed with a lifetime of 10 ns.
Figure 5:
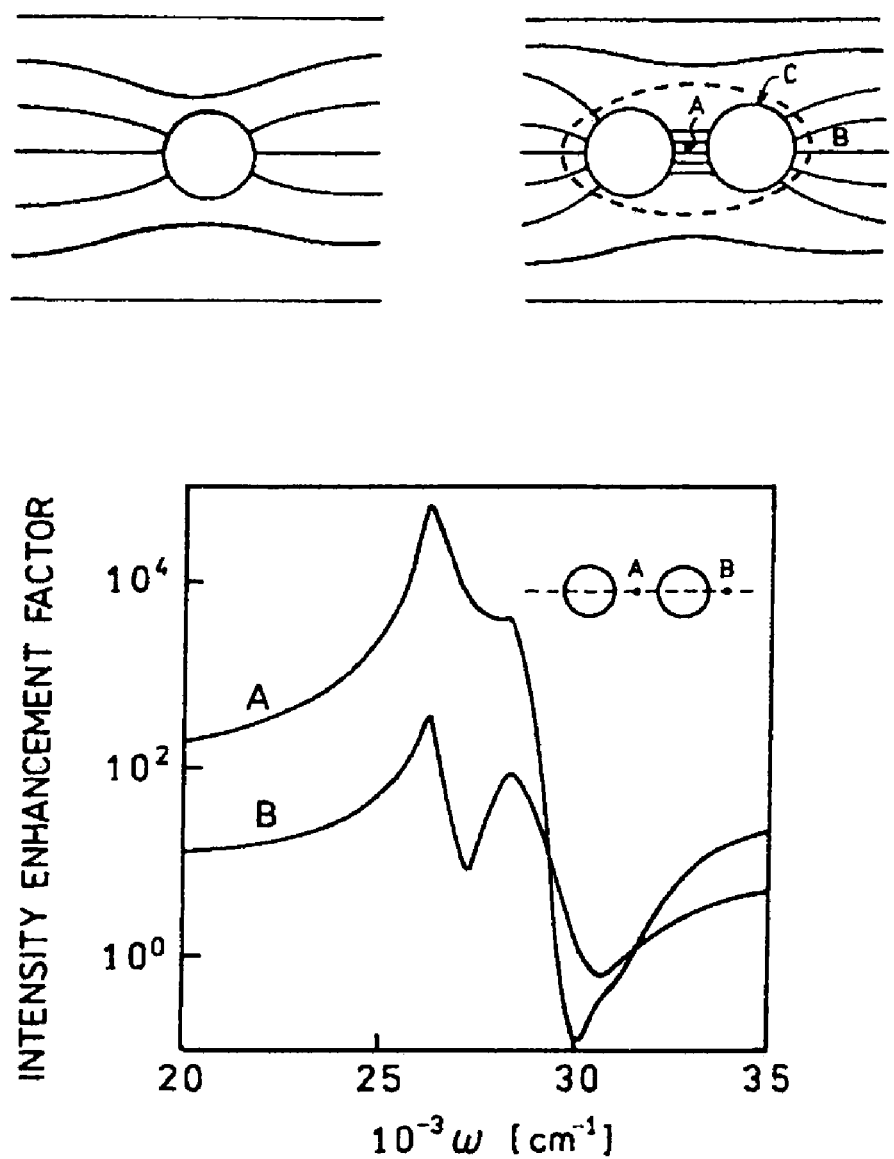
FIG. 5 illustrates an electric field around a spheroid and between two spheroids. Points A and B have the highest fields, and point C has the lowest field. The lower panel shows the local intensities at points A and B.
Figure 6:
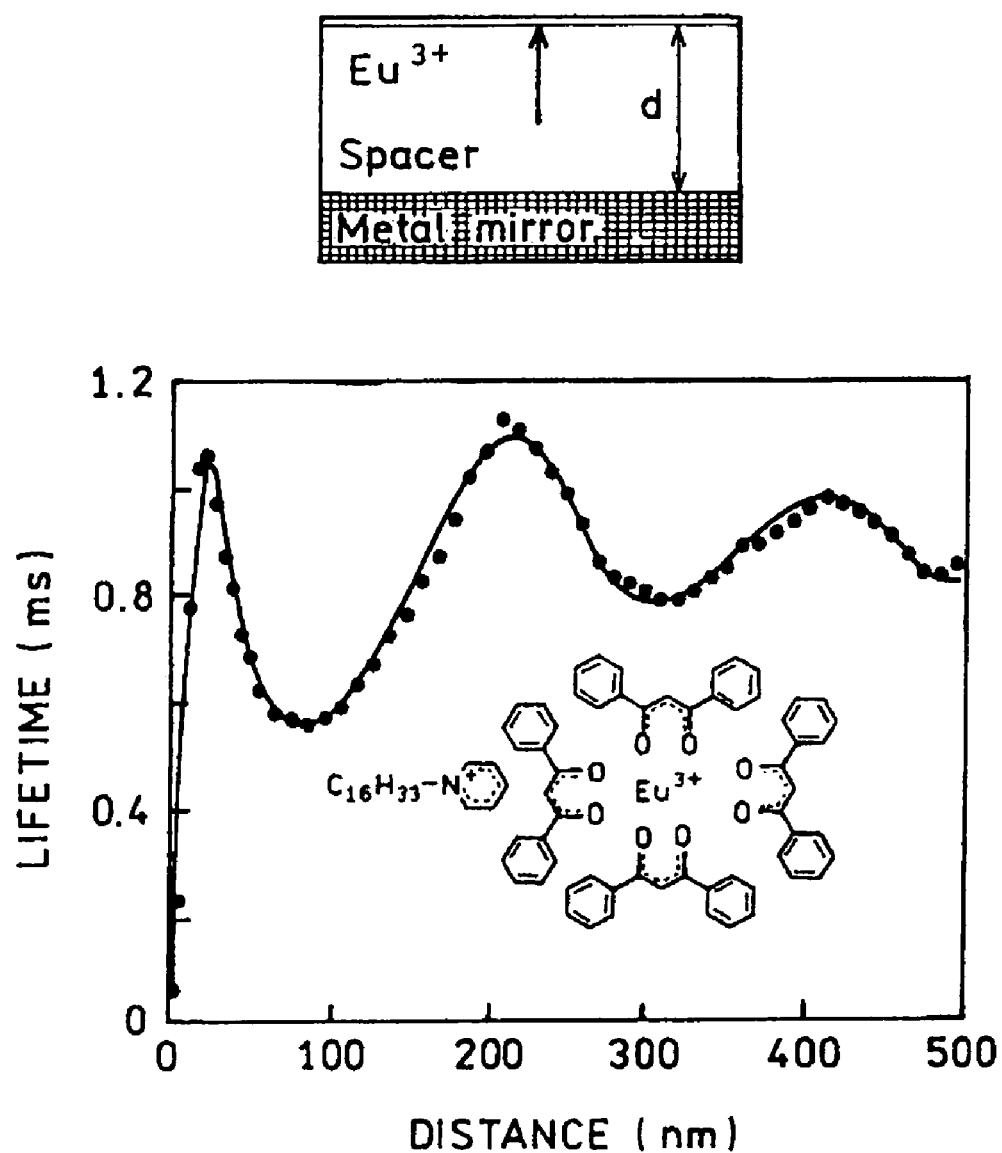
FIG. 6 illustrates the lifetime of $Eu^{3+}$ ions in front of an Ag mirror as a function of separation between the $Eu^{3+}$ ions and the mirror. The solid curve is a theoretical fit.
Figure 7:
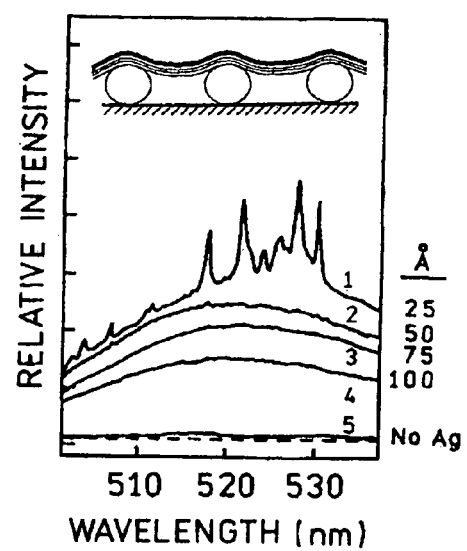
FIG. 7 illustrates the fluorescence decay of $Eu^{3+}$ ions.
Figure 7:
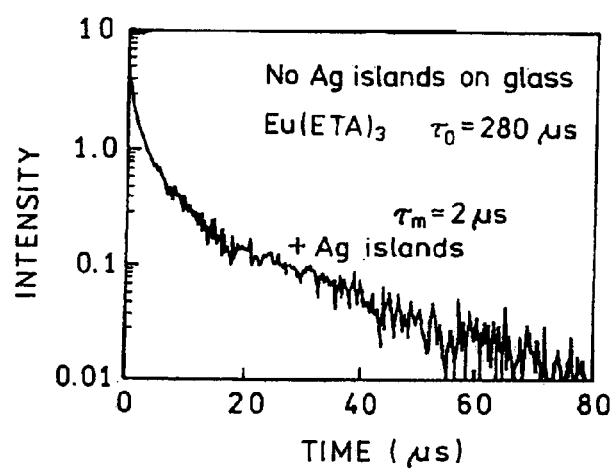
Figure 8:
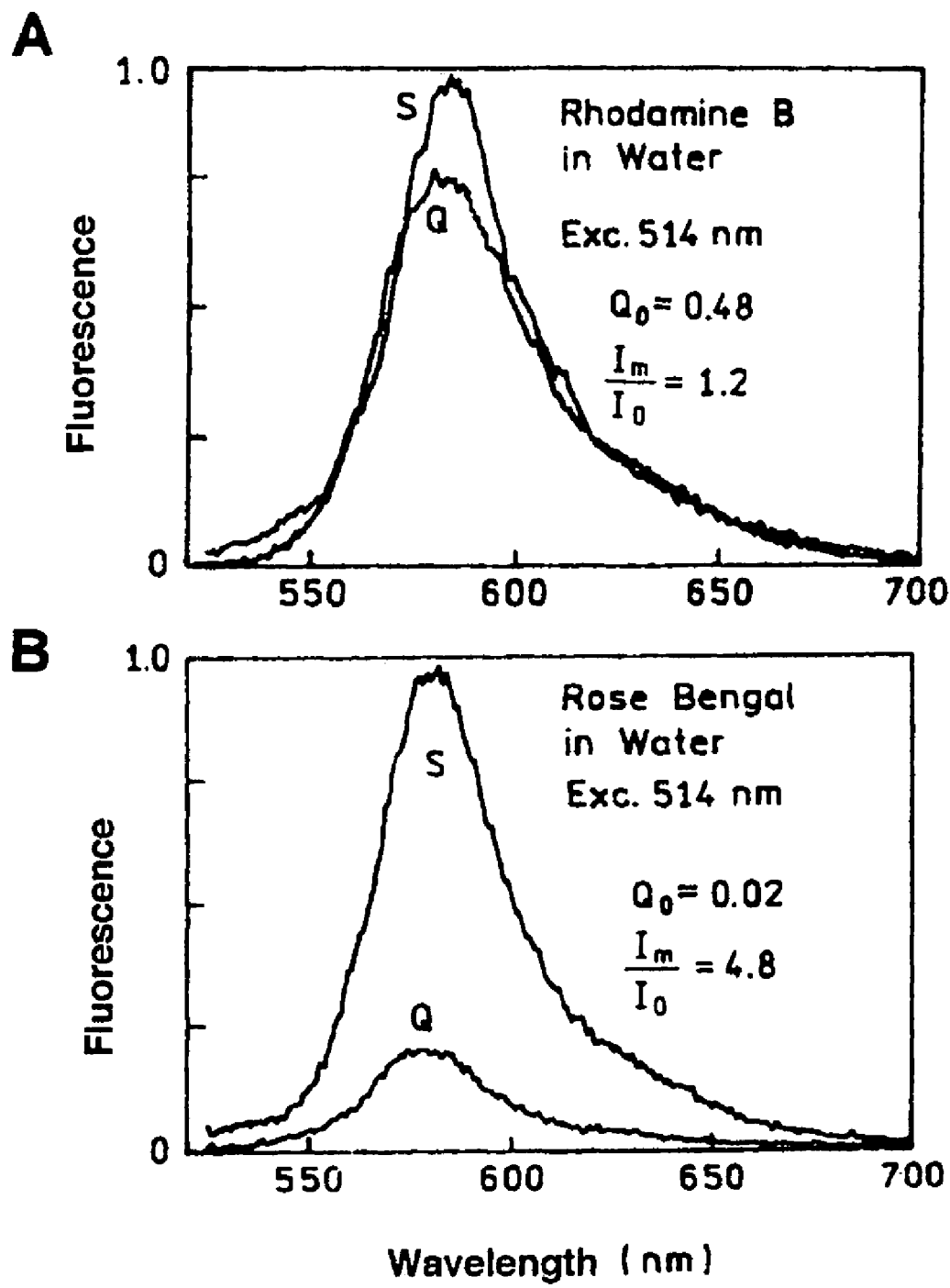
FIG. 8 illustrates the fluorescence intensity of A) rhodamine B; and B) rose Bengal, in the presence and absence of quartz slides. S=silver and Q=quartz.
Figure 9:
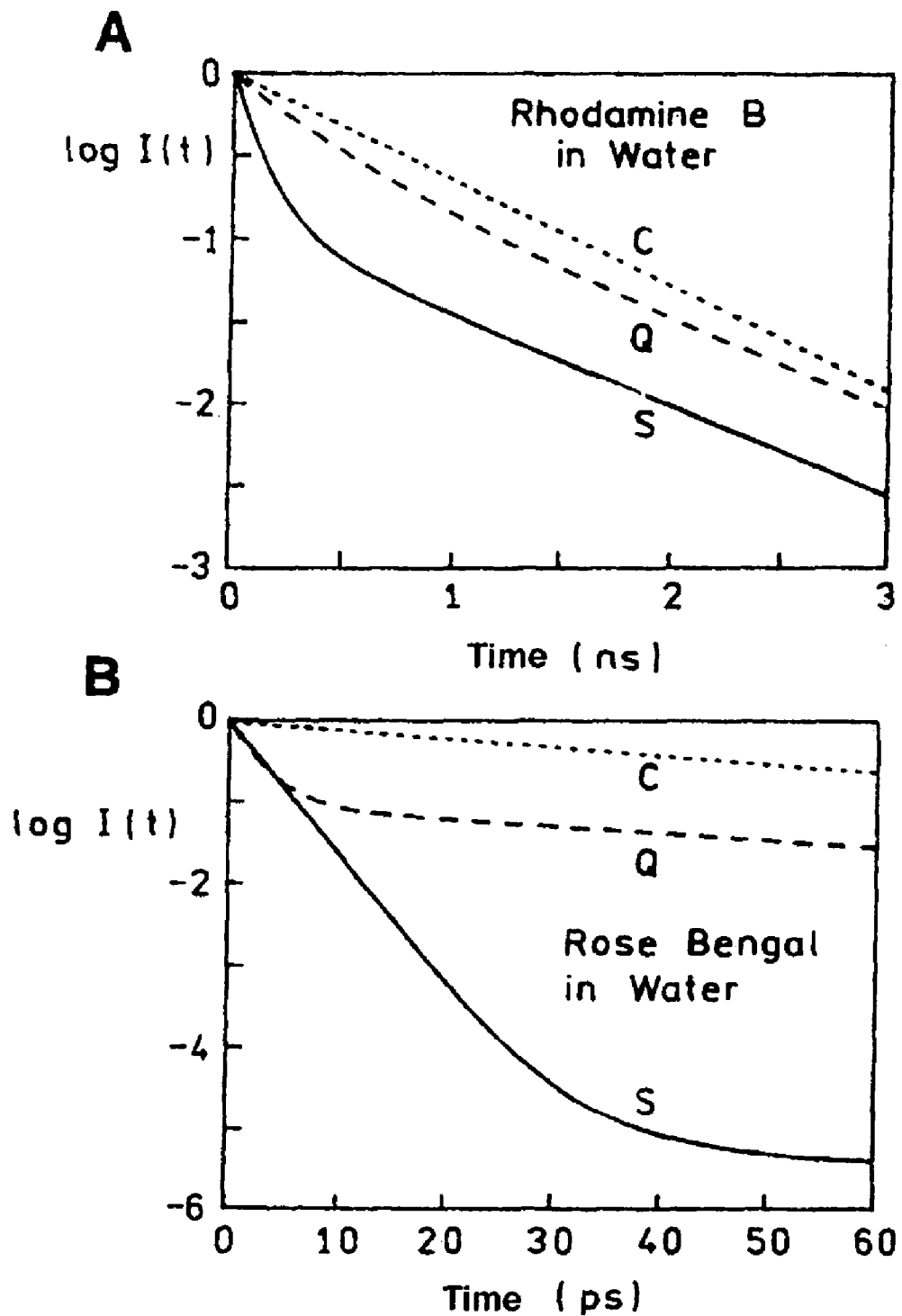
FIG. 9 illustrates the intensity decays for A) rhodamine B and B) rose Bengal in Cuvettes, C between unsilvered quartz slides (Q) and between silvered quartz slides (S).

These equations result in important predictions for a fluorophore near a metal surface. As $\Gamma_m$ increases, the fluorescence quantum yield increases while the lifetime decreases, as shown in FIG. 4, which is converse to the free space condition where both change in unison. An ability to modify and control the radiative decay rate ($\Gamma+\Gamma_m$) can have profound implications for the use of fluorescence in basic research and its applications.

The plots in FIG. 4 have been calculated using equation (3), assuming three fluorophores with a good (0.5), low (0.1) and very low quantum yield (0.01). The largest enhancement in quantum yield is observed for weak fluorophores. It is realistic to envisage fluorophores with quantum yields of about 0.001 (practically non fluorescing) that become highly fluorescent (quantum yield ~1.0) near a metal surface, with a maximum enhancement factor of $1/Q_0$. In terms of assay development of the present invention this is a most attractive phenomenon, as the capture of the target DNA (by a labeled complementary strand, see FIG. 1) will result in significant fluorescence emission, while the bulk solution remains dark. The second favorable lightning rod effect also increases the fluorescence intensity through locally enhanced excitation. In this case, emission of fluorophores can be substantially enhanced irrespective of their quantum yields.

The reduction in lifetime of a fluorophore near a metal is due to an interaction between fluorophore and metal particle, which enhances the radiative decay rate (quantum yield increase) or depending on distance, $d^{-3}$, causes quenching. FIG. 4 (right) shows, the effect of modifying the radiative decay rate on the fluorescence lifetime. For the calculations, Equation (4) was used assuming a free space lifetime of 10 ns. It should be note that lifetimes of fluorophores with high quantum yields (0.5) would decrease substantially more that the lifetimes of those with low quantum yields (0.1 and 0.01). A shorter excited-state lifetime also allows for less photochemical reactions which subsequently results in increased fluorophore photostability.

Fluorophore photostability is a primary concern in many applications of fluorescence. This is particularly true in recent trends in single molecule spectroscopy. A shorter lifetime also allows for a larger photon flux. The maximum number of photons that are emitted by a fluorophore each second is roughly limited by the lifetime of its excited state. For example, a 10 ns lifetime can yield about $10^8$ photons per second per molecule, but in practice only $10^3$ photons can readily be observed [15]. The small number of observed photons is typically due to both photodestruction and isotropic emission. If the metal surface decreases the lifetime then one can obtain more photons per second per molecule by appropriately increasing the incident intensity. On the other hand, the metal enhanced fluorescence effects of the present invention enhances intensity while simultaneously shortening the lifetime. Decreases in the excitation intensity will still result in increases in the emission intensity and therefore photostability.

The ability to increase the radiative decay rate suggests that any chromophore, even non-fluorescent species such as bilirubin, fullerenes, metal-ligand complexes or porphyrins could display usefully high quantum yields when appropriately placed near a metal surface.

The effects of metal surface-fluorophore interactions are highly dependent upon distance and the nature of the metal surface. The emission enhancement is observed when fluorophore distances near 5-50 nm to the metal surfaces, c.f. FIG. 2. At this scale there are few phenomena that provide opportunities for extremely high levels of assay-sensing, manipulation, and control. In addition, devices at this scale may lead to dramatically enhanced performance, sensitivity, and reliability with dramatically decreased size, weight, and therefore cost, important considerations for field-deployable bioterrorism anthrax sensors. Slightly different effects can be expected for mirrors, sub-wavelength or semi-transparent metal surfaces, silver island films or metal colloids [32].

In one preferred embodiment of the present invention, a fluorophore is positioned between multiple silver colloids. In the assay of the present invention, (FIG. 1, assay 2) at least one silver colloid is located at one end of the fluorophore-labeled free complimentary capture strand of DNA. Upon hybridization with the target DNA sequence, the fluorophore will be positioned in this high electric field region between the colloids. The high field enhances the emission of the high or low quantum yield fluorophore label. The high-field further enhances the extent of multiphoton excitation of the fluorophore.

As part of the anthrax assay of the present invention, sequences with specificity for the anthrax toxin gene PA (protective antigen) were used, and further it is noted that a bioinformatics approach may be used to identify additional, unique, chromosomally located, Anthrax specific target sequences.

The possibility for altering the radiative decay rate was demonstrated by measurements of the decay times of europium ($Eu^{3+}$) positioned at various distances from a planar silver mirror using Langmuir-Blodgett films [51-54]. In a mirror the metal layer is continuous and thicker than for a semi-transparent film. The lifetimes of $Eu^{3+}$ oscillate with distance from the metal yet still remain a single exponential at each distance, as shown in FIG. 6. The oscillating lifetime can be explained by changes in the phase of the reflected field with distance and the effects of the reflected field on the fluorophore [21]. A decrease in lifetime is found when the reflected field is in phase with the fluorophore. As the distance increases, the amplitude of the oscillations decreases. At short distances, below 5 nm, the emission is quenched, c.f. FIG. 2. This effect is due to a coupling of the fluorophore dipole to the surface plasmon resonances of the metal, oscillating surface charges on the metals surface. The lifetimes typically oscillate at around 25% the free space value. However, more dramatic effects are seen with small metal particles, as shown in FIG. 7. Here silver islands were coated with a thin film of Eu $(ETA)_3$, where ETA is a ligand that chelates europium. When the $Eu^{3+}$ chelate was deposited on a silica substrate without the silver islands, it displayed a single exponential decay time of 280 μs and a quantum yield near 0.4 ($Q_0$ is typically 0.4). However, when deposited on silver island films, the intensity increased about 5-fold (not shown) and the lifetime decreased by ca. 100 fold to near 2 μs, as shown in FIG. 7.

Also the decay is no longer a single exponential on the silver island films [55]. The silver islands had the remarkable effect of increasing the intensity 5-fold while decreasing the lifetime 100-fold. Such an effect can only be explained by an increase in the radiative decay rate, c.f. equations 3 and 4. In this sample geometry an inert coating between the islands prevented $Eu^{3+}$ chelates between the islands from being emissive. The 5-fold increase in the quantum yield of $Eu(ETA)_3$ resulted in an apparent quantum yield of 2.0, which by definition is impossible. Hence this additional enhancement must be due to an increase in the local excitation field ($E_m$ on FIG. 2) near the metal particle. It should be noted for clarity that this increase in local intensity of the incident light cannot explain the decreased lifetime, because an unperturbed $Eu^{3+}$ chelate excited by this enhanced field would still decay with a 280 μs lifetime, i.e. enhanced excitation results in a visual increase in fluorescence and does not alter the fluorescence lifetime. Interestingly, these large increases in the radiative decay rate are due to fluorophores near metallic particles.

It was found that dramatic increases occur for metallic colloids rather than planar-mirrored surfaces. For example, Raman signals are dramatically enhanced by metal colloids or islands [56,57]. Surface enhanced fluorescence was investigated by using low (Rose Bengal $Q_0$=0.02) and high quantum yield fluorophores (Rhodamine B, RhB, $Q_0$=0.48) and silver island metal films, as shown in FIGS. 8 and 9. Silver island films were made by depositing silver on a glass substrate and consist of sub-wavelength size silver particles. Under appropriate conditions the glass becomes covered with circular islands about 200 Å in diameter. About 40% of the surface is typically covered by the silver. FIG. 10 shows the experimental geometry used for collecting this data. For RhB the intensities are nearly equivalent between two unsilvered quartz plates (Q) and between the silver island films (S). The small enhancement of RhB, shown in FIG. 8 is expected because for high quantum yield fluorophores the radiative rate cannot be substantially increased, where the quenching interaction with the metal and the excitation enhancement effects are likely to compete. If there is an excitation enhancement effect in this sample then it is thought to be offset by the quenching effect, $k_m$. In any event the emission intensity increased for Rose Bengal (the lower quantum yield species) and this excitation enhancement is present during the excitation of both RhB and rose bengal. For rose Bengal, a remarkable 5-fold increase in intensity was observed as shown in FIG. 8B. This increase is especially remarkable when it was recognized that only a small fraction of the volume between the films is within this enhancing region. This interaction region is expected to extend to a minimum of 200 Å into the solution. Given the 1 μm thickness and the presence of two films, only about 4% of the sample can be within this enhancement region. This suggests a very high quantum yield for rose bengal molecules adjacent to the surface (greater than unity), which can only be explained by a complimentary increase in the rate of excitation also, $E_m$, FIG. 2. Lifetime measurements are also informative as shown in FIG. 9, as the intensity measurements shown in FIG. 8 might under normal circumstances be explained by an increased rate of excitation or enhanced fluorescence due to the fluorophore binding to the surface of the quartz. However, lifetime measurements are unambiguous and show a substantial reduction in lifetime for rose bengal between silvered quartz plates, where as RhB lifetime remained roughly constant. The slight drop in RhB lifetime can be explained by some RhB molecules being within 50 Å of the silver and hence are quenched. The bi-exponential decays can be explained in terms of sample heterogeneity.

Several other fluorophores of different well-characterized free space quantum yields were examined, including Erythrosin B, $[Ru(bpy)^2]^2$+, Basic Fucisin, : $[Ru(phn)_2dppz]^{2+}$ as shown in FIG. 11. In all cases it was found that the largest enhancements with the lowest quantum yield fluorophores, confirming our predictions of enhanced fluorescence due to both an increase in radiative decay rate and enhanced excitation. These results were performed on silver island films, formed by a chemical reduction on the quartz surface, which are relatively simple to fabricate.

Figure 10:
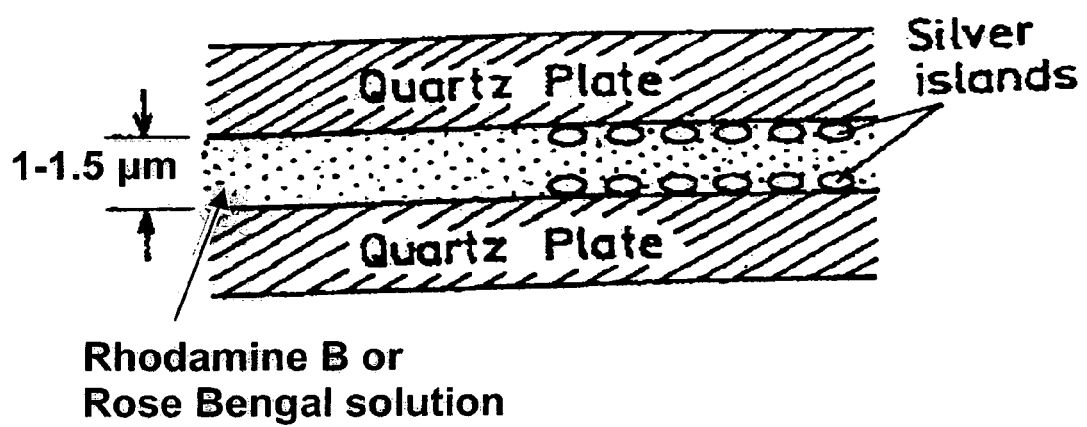
FIG. 10 illustrates a sample geometry of silver island films of sub-wavelength size silver particles. Under appropriate conditions the glass becomes covered with circular islands of silver about 200 Å in diameter. About 40% of the surface is typically covered by the silver and the distance of the fluorophores from the silver surface is controlled.
Figure 11:
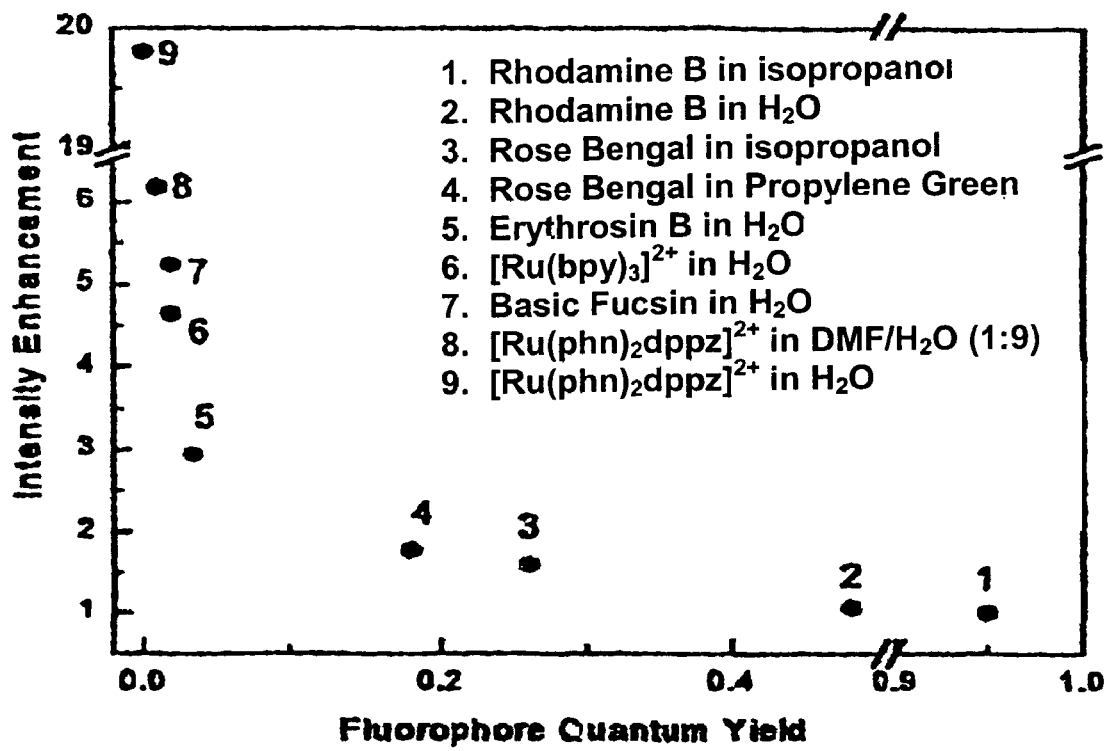
FIG. 11 shows the enhancement in fluorescence intensity for several fluorophores.
Figure 12:
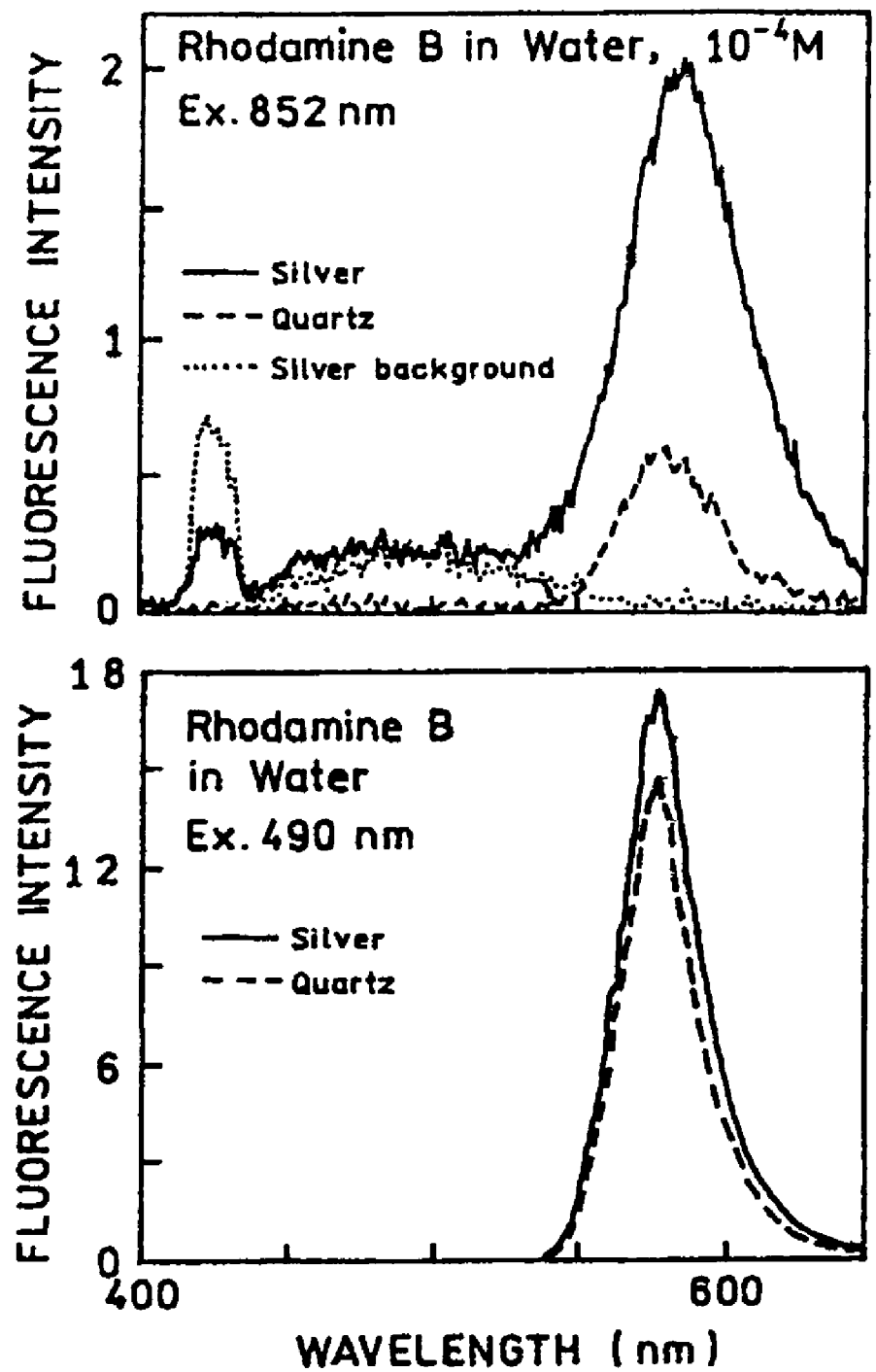
FIG. 12 illustrates (Top) 2-photon excitation and (Bottom) 1-photon excitation of RhB in the sample geometry shown in FIG. 10.

Complimentary to above discussed 1-photon results and interpretations, it was shown localized two-photon excitation of Rhodamine B (RhB) fluorescence occurring near metallic silver islands increases fluorescence emission intensity. This increase, as shown in FIG. 12, is accompanied by a reduction in lifetime as compared to that observed using 1-photon excitation. Given the high quantum yield of RhB ($Q_0$=0.48) these results can be explained by the metallic particles significantly increasing the excitation rate, $E_m$, of the RhB molecules. Moreover, given the sample geometry of FIG. 10, and the absence of any notable increase in emission intensity using 1-photon excitation, as well the fact that the 1-photon mean lifetime remained essentially unchanged both in the presence and absence of silver, suggests that enhanced 2-photon excitation is localized to regions in close proximity to the silver islands.

Figure 13:
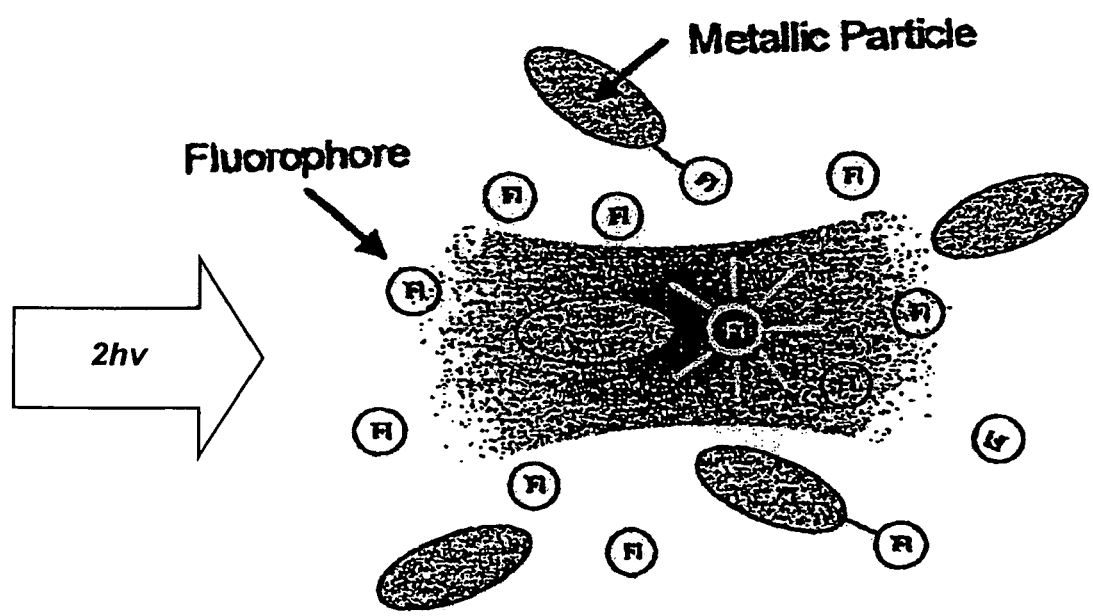
FIG. 13 illustrates the preferential multiphoton excitation of fluorophores in close proximity to metal, in the presence of free fluorophores, FL.

In addition to metallic particles and/or colloids modifying a fluorophores radiative decay rate, they are also known to increase excitation rates by concentrating the incident light [59,60]. The maximum enhancement in the incident electric field has been calculated to be a factor of 140 in the vicinity of appropriately sized metallic ellipsoids [61]. Since the incident intensity is the square of the incident field strength then for a 1-photon process, enhancements in excitation rates by a factor of up-to $2\times10^4$ are possible. It is this phenomenon that one can typically attribute to increases in observed apparent quantum yields near metallic particles to greater than unity. However, a much more dramatic enhancement is possible for multiphoton excitation. For a two-photon absorption process the rate of excitation is proportional to the square of the incident intensity. This suggests that two-photon excitation could be enhanced by a factor of $3.8\times10^8$. Such an enhancement in the excitation rate is thought to provide selective excitation of fluorophores near metal islands or colloids, even if the solution contains a considerable concentration of other fluorophores that could undergo two-photon excitation at the same wavelength, but are more distant from the metals surface, FIG. 13. This interpretation is substantiated by the fact that given the overwhelming excess of high quantum yield RhB in this geometry (96% of solution is too distant for any fluorophore-metal effect) the fluorescence lifetime is still shorter than that typically observed for bulk solution RhB in the absence of metal.

For the surface anthrax assay described herein and shown in FIG. 1, two-photon excitation enhances the fluorescence of the label when bound to the target strand but additionally excludes any fluorescence signal from the bulk solution. This increases the signal to noise ratio of the system, substantially increasing the likely detection of a single strand of anthrax DNA.

Figure 14:
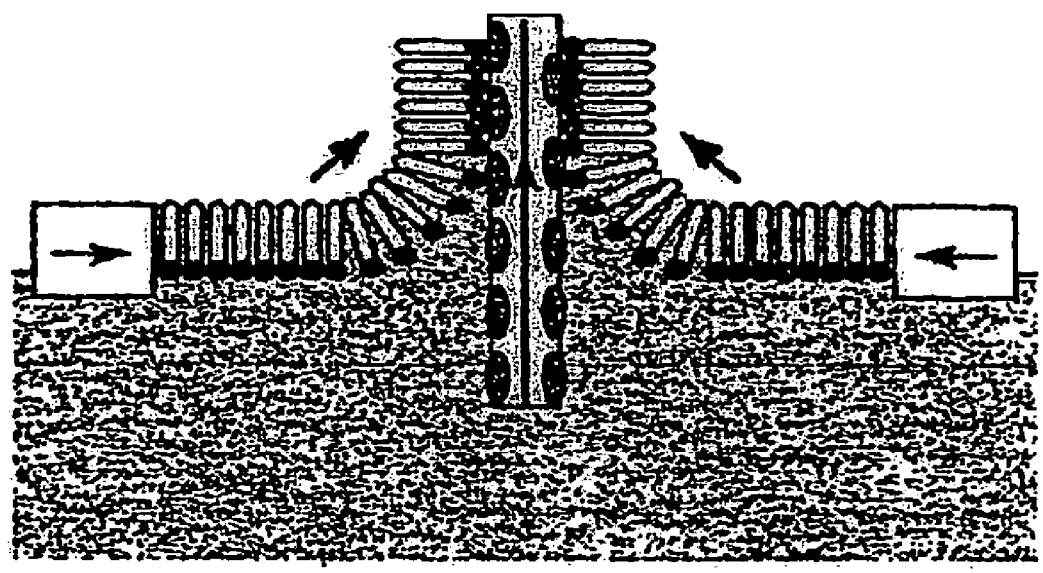
FIG. 14 illustrates the Langmuir-Blodgett technique for depositing the first monolayer of fatty-acid spacer onto two back-to-back silvered quartz slides.
Figure 15:
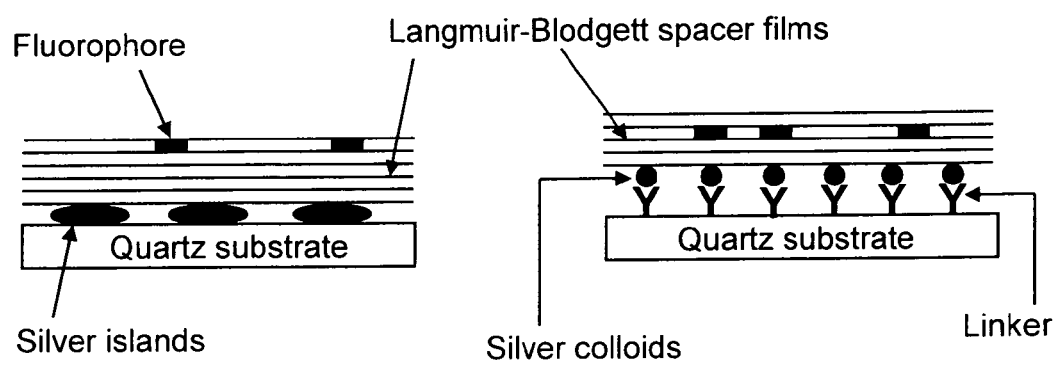
FIG. 15 illustrates an experimental geometry that can be utilized to investigate the distance dependence of Metal-Enhanced Fluorescence (MEF).
Figure 16:
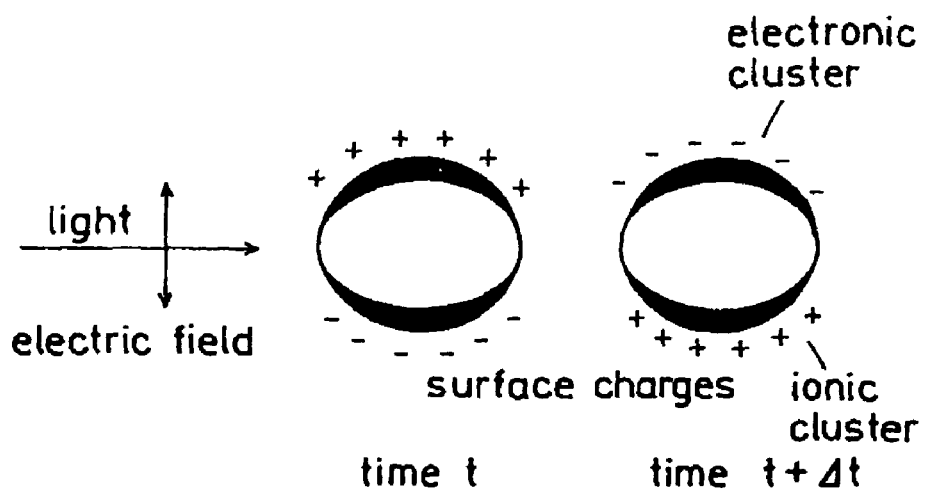
FIG. 16 illustrates absorption spectra of gold colloidal spheres.
Figure 16:
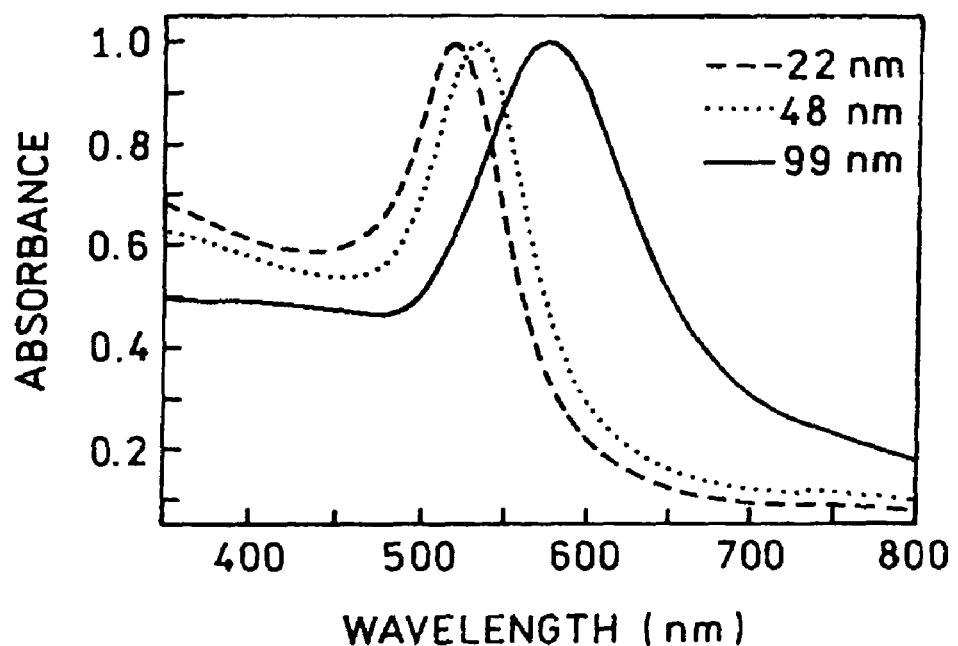
Figure 17:
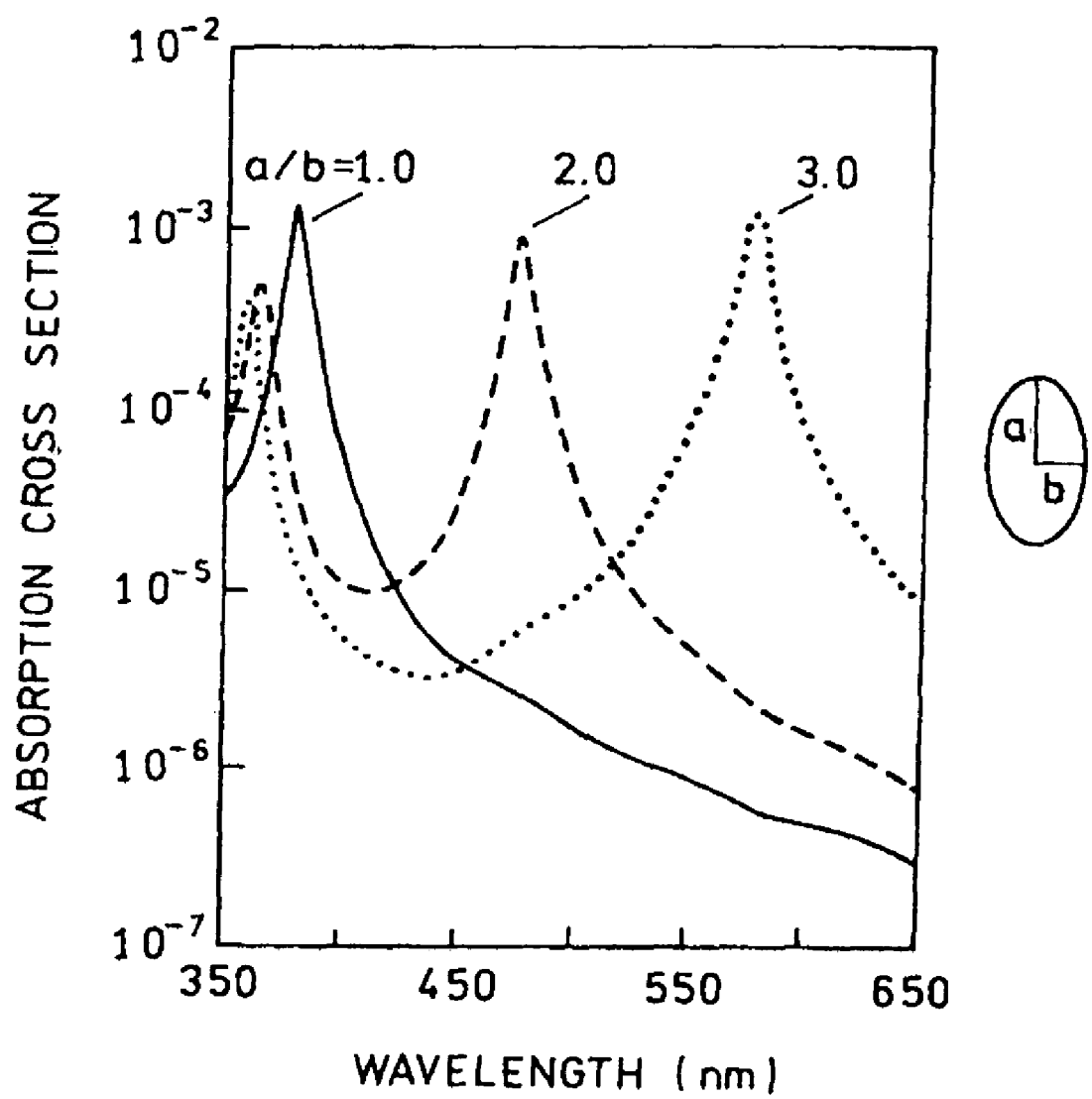
FIG. 17 illustrates absorption cross-section for a silver sphere in water (–) and for prolate spheroids with axial ratios of 2.0 and 3.0 in the small particle limit.

Fluorophores can undergo a finite number of excitation and emission event cycles prior to photodecomposition. This is a particularly important consideration in single molecule detection and fluorescence microscopy, where the signal level is limited by photodecomposition. For photostable molecules like tetramethyl-rhodamine, photodecomposition occurs after about 105 event cycles, where less stable fluorophores will degrade after significantly fewer event cycles.

The $d^{-3}$ quenching effect which occurs for fluorophores positioned less than 50 Å close to the surface will be first considered. Assuming there is no change in the radiative rate, $\Gamma_m$=0, the emission intensity will decrease due to quenching near the surface. However, it is known that quenching by RET results in increased photostability, because the fluorophores spend less time in the excited state, avoiding potential opportunities for photochemical reactions. Given the increase in photostability, the fluorophore can undergo more excitation/emission event cycles prior to photodecomposition, but the reduced quenched lifetime can cancel out this effect, resulting in a similar number of observed photons or fluorophore detectability.

Suitably fabricated metallic particles, with regard to shape and size, can result in a maximum 140-fold amplification of the local intensity [59], which is likely to result in a larger observed fluorescent-intensity at a given illumination. Given that the radiative rate is not altered, then the lifetime will remain the same. Also, since there is no quenching (lifetime remains unchanged), essentially the same overall number of photons will be emitted until the fluorophore degrades. One possible effect is that the fluorophore may display ground state depletion at lower incident intensity of the excitation light. Since the intensity is proportional to the squared field strength, appropriately designed metallic particles may result in an additional 10,000-fold increase in fluorescence intensity. Enhanced excitation rates are likely to increase the extent of fluorophore photodecomposition. Moreover, given the enhancements, it may be expected that the same emission intensity will be observed from fluorophores, but by using a 10,000 times weaker power excitation source, which may be desirable in some biological assay studies.

Further, it has been predicted that the location of a fluorophore at a suitable distance from a metallic surface can result in over a $10^3$ increase in radiative decay rate which at the same illumination intensity and combined with an enhanced excitation rate, would produce a remarkable cumulative $10^7$ increase in fluorescence intensity. In terms of photostability and detectability, an increase in the radiative decay rate is expected to result in dramatic increases in the number of photons observed from each fluorophore. The decreased lifetime is expected to increase the photostability of fluorophores and therefore allow a greater excitation/emission cyclic rate. Hence the combined effect of an increased quantum yield and reduced fluorescence lifetime would result in substantially more detected photons per fluorophore.

Finally, directional emission, which can be characteristic of surface enhanced fluorescence would allow for an additional factor of 10 or more, (typical spectrofluorometers only detect about 1% of all isotropic fluorescence emission [30]), which combined with a further potential 100 fold enhancement when using two-photon excitation, enhancements of $10^{10}$ in fluorescence emission intensity may be observed. Using an appropriately optimized silver surface-fluorophore geometry and appropriate assay washing, single capture events (DNA binding) are detectable.

Fabrication of silver islands and silver colloids deposited on quartz slides (low background), with fluorophores positioned at known distances above the metal was accomplished using Langmuir-Blodgett films. Measurements of the metal-fluorophore distances are obtained by using fatty acid spacers such as arachidic acid ($C_{19}H_{39}COOH$), and by using spin coated polymer films such as polyvinyl alcohol (PVA). Polymer film thickness is determined using simple absorbance measurements and ellipsometry. Coordinating specific enhancement distances for standard fluorophores with specific oligonucleotides (distance), optimal fluorescence enhancement is achieved.

The Langmuir-Blodgett technique provides the most accurate way of controlling film thickness and surface uniformity and was used to obtain the data for $Eu^{3+}$ in FIG. 6 [51-54]. This technique allows for accurate control of the short-range metal-fluorophore distance and hence allows the distance dependence of surface enhanced fluorescence to be quantitatively characterize. Different numbers of fatty add layers, with an additional final layer containing the desired fluorophore were laid down using a KSV 5000 III. Alterative Layer Dipping Trough (KSV Instruments, Inc.) was used to measure for optimal fluorescence enhancement distance, FIGS. 14 & 15. While the thickness of these monolayers is well characterized [51], ellipsometry, which measures the phase difference in the polarization of linearly polarized light on reflection from a surface was used to additionally confirm the thickness of the fatty acid layers [63]. The length of the complimentary capture anthrax DNA strand used for the assay was based upon positioning a fluorophore at known geometries with the specific distance dependence of MEF from a surface of silver islands and/or colloidal films.

Another method to vary the long-range distance-dependence of surface enhanced fluorescence is the use of spin coated poly-vinyl alcohol films. This routine technology readily allows for films to be coated onto a variety of surfaces, with varying thickness from >0.1 μm [68,69].

The silver surfaces required for MEF are obtained using silver metal island films, sandwiched films as shown in FIG. 10, or even spin coated silver islands or colloids. A quartz surface is preferably used for forming the metal islands. Prior to use the quartz slides were soaked in 10 parts 98% $H_2SO_4$ and 1 part 30% $H_2O_2$ for at least 24 hrs. The silver island particles were prepared in clean beakers by reduction of silver ions using various reducing agents [70]. Sodium hydroxide was added to a rapidly stirred silver nitrate solution forming a brown precipitate. Ammonium hydroxide was added to redissolve the precipitate. The solution was cooled and dried quartz slides were added to the beaker, followed by glucose. After stirring for 2 mins the mixture was warmed to 30° C. After 10-15 min the mixture turned yellow-green and became cloudy. A thin film of silver particles formed on the slides as could be seen from their brown-green color. The slides were rinsed in pure water prior to use. Additional procedures for preparing silver and gold particles are also available [71-75], with silver preferred over gold because of the longer surface plasmon absorption of gold, which accounts for its familiar color. Slides were silanized by placing them in a 2% solution (v/v) of 3-aminopropyltrimethoxysilane (APS) in dry methanol for 2 hrs, rinsing and then air-drying. The silanized substrates should be used within one hour or stored under a dry nitrogen atmosphere. The use of fresh silver surfaces should be used to avoid oxidation or other chemical reactions on the surface. Surface plasmon absorption is used to monitor the quality of the islands and all assay surfaces.

Colloids may be prepared as suspensions by citrate reduction of silver or gold. Silver particles are preferably used with shorter wavelengths [76]. Gold colloids can be used with longer wavelength red and NIR fluorophores. Since there is extensive literature on the optical properties of metal particles [77,78] and the effects of interface chemistry on the optical property of colloids [79], the size of the colloids and their homogeneity are readily determined. It is also possible to prepare bimetallic metal nanoparticles [80] or hollow sphere colloids [81]. For a hollow sphere, a fluorophore is positioned in the center of the silvered sphere, which is transparent to the fluorescence emission.

Additionally, pre-formed metal particles or colloids can be bound to glass surfaces by placing functional groups such as cyanide (CN), amine ($NH_2$), or thiol (SH) on a glass or polymer substrate. Silver and gold colloids spontaneously bind to such surfaces with high affinity [82,83]. Colloids bound to the glass surface can then be coated with either Langmuir-Blodgett spacer films or spin-coated PVA to investigate the fluorescence enhancement as a function of distance from the surface. It was found that significant enhancements occur when using glass-bound silver colloids as compared to silver island films. Both silver island and silver colloid films can also be stabilized to reduce long-term oxidation, which reduces the surface plasmon resonances. APS may be used to grow an inert $SiO_2$ layer, from TMOS (Tetramethylorthossilicate) to reduce surface oxidation. The $SiO_2$ coating not only protects the surface, but also maintains the silver surface plasmon resonance's of silver, where only a slight shift in surface plasmon absorption is observed. If desired the silica can then be derivatized by methods used for attaching organic molecules to glass [84]. Further procedures for coating particles with silica have also been developed [85,86].

Surface plasmon absorption is due to the oscillations of free charges at a metal boundary which propagate along the metal surface. These resonances are often excited using evanescent waves. The surface plasmon absorption can give an indication of colloid size, FIG. 16, and shape, FIG. 17. Surface plasmon absorption effects depend on the refractive index of the medium and under certain conditions it is sensitive to compounds binding to the surface of the metal [26,27], where any effects of binding on the surface plasmon absorption can be monitored using simple absorption measurements. In addition other methods to protect the plasmon absorption of metal surfaces and colloids are known in the art, i.e. by coating with polyvinylpyrrolidone (PVP) [96], and may be used if required.

For detection of a specific single anthrax DNA sequence, one of the DNA oligonucleotide capture sequences is immobilized to the metal or silica (protective layer) surface, as shown in FIG. 1. Thiol-containing oligonucleotides are linked to slides treated with (3-mercaptopropyl) trimethoxysilane (MPTS) [87,88] or N-(6-maleimidocaproxy)succinimide (EMOS) [89]. The sulfhydryl-groups spontaneously bind to silver and gold and the plasmon resonance is retained [90,91]. Amino groups are used to spontaneously bind amino-terminated oligonucleotides to silver [92]. Similar methods are available to attach silver or gold colloids to glass substrates [93,94], some using avidin-biotin chemistry [95].

The design of the silver micro-arrays used to detect Anthrax (as shown in FIG. 1). The first assay uses immobilized silver particles on a quartz substrate. The second assay makes use of the additional colloids for superior fluorescence enhancement emission when the fluorophore is positioned between the colloids.

As discussed above, DNA oligonucleotides may be bound to silver surfaces or particles by using amino or sulfhydryl groups using methods known in the art. The length of the complimentary capture DNA oligonucleotides are determined by the metal enhanced fluorescence experiments with the Langmuir-Blodgett films and spin coated PVA. Suitable DNA sequences for use in the assay are those DNA sequences that bind the 2nd complimentary strand out of the quenching region (>50 Å, FIG. 1) but still within the enhancement region (50-500 Å). Fluorophore-metal distances which provide maximum fluorescence enhancement are determined empirically and are thus used in determining the DNA sequence length to use for DNA capture sequences so that fluorescence of same is optimally enhanced While any fluorophore can be used for the assay system, low quantum yield fluorophores are more desirable because: 1) they produce a greater fluorescence enhancement and therefore increase detectability [26-30] and; 2) the background of the assay is darker, producing a better signal-to-noise ratio and thus provides better assay sensitivity. Also, in using 2-photon excitation for the assay [97-99], fluorescent probes with good 2-photon cross-sections [100] are desirable. Rhodamine 6G and Fluorescein are readily used as 2-photon probes [101] and nucleotides for oligonucleotide synthesis are available labeled with these two fluorophores.

The fluorophores are placed in specific locations (distances which provide optimal metal enhanced fluorescence), by incorporation of labeled nucleotides during solid state oligonucleotide synthesis. Alternatively, labeled nucleotides are incorporated using PCR or various methods well known in the art.

Using an inert $SiO_2$ surface coating reduces oxidation effects while still maintaining the surface plasmon absorption of the metal. To reduce oxidation effects, fresh colloids may be coated with inert silica from sol-gel solutions using known procedures [102]. Silane reagents will subsequently place reactive groups on the surface where capture DNA oligonucleotides are attached, as shown in FIG. 1. Additionally, the $SiO_2$ coatings themselves are used as inert spacers for MEF.

A panel of B. anthracis isolates are assembled and stored as spore preps at −70° C. in 15% glycerol broth until required. A panel of other members of the B. cereus group are also assembled and stored at −70° C. in 15% glycerol broth until required. This panel contains representatives of strains that in the past have cross-reacted with anthrax specific sequences. When vegetative organisms are required the strains are cultured in brain-heart infusion agar and checked for purity by subculture onto blood agar plates.

Bacterial DNA may be isolated using various DNA isolation methods known in the art. A kit suitable for isolating DNA is the Roche High Pure PCR Template Preparation Kit. DNA concentration is estimated by measuring the absorbance of a solution at 260 nm. An $A_{260}$ value of 1 is equivalent to a DNA concentration of 50 μg/ml for double stranded DNA and 20 μg/ml for single-stranded DNA. The purity of a sample is assessed by calculating the 260/280 nm absorbance ratio. This is approximately a ratio greater than 1.5 for protein-free DNA samples.

Oligonucleotide sequences should be examined to ensure that the nucleotide sequence does not contain self-complementary stretches that could potentially form stem loops. Complementarity between oligonucleotide pairs is also avoided as this can lead to formation of primer-dimer artifacts. Binding of the oligomer to other regions of the template DNA is avoided by prior comparison of the DNA nucleotide sequence of the template DNA to be amplified for local high percentage match to the primer, using the PRIMER EXPRESS software package from Perkin Elmer ABI. The step of washing the assay surface after target capture will remove any non-hybridized complimentary labeled capture stands if the background fluorescence signal levels from the bulk solution are high.

Previously designed PCR primers used to determine the nucleotide sequence of PA [103] serve as a starting point for the design of oligomers [104].

When compared to other completed bacterial genomes, most B. anthracis proteins have their highest level of similarity to other Bacillus genomes (B. subtilis (2065 (36%)) and B. halodurans (1082 (19%)). Most B. anthracis chromosomal proteins have homologs in the draft sequence of the B. census 10987 genome (this is currently being undertaken by TIGR), confirming the very dose relationship between these organisms. There are 642 genes in B. anthracis without matches in B. subtilis, B. halodurans or B. census 10987, but these are mostly small hypothetical proteins. Only 43 have a predicted function, and these numbers may be lower when the completed B. cereus 10987 genome is available. These genes may define unique phenotypic characteristics of B. anthracis, which could be potentially of great interest in regard to virulence. Using this information immobilized and free DNA oligonucleotides used for probes are designed and screened for sensitivity and specificity for their target sequence.

The surface anthrax assay can use 2-photon excitation at approximately 750-900 nm using short pulse width (<50 ps), high repetition rate (>1 MHz), laser diode sources. Due to the significant enhancements in the excitation rates of fluorophores near metallic surfaces, $E_m$, (FIG. 2) the fluorescence enhancement of the one-photon optimized system (i.e. where the distance dependence was predetermined by L-B films) can be reevaluated with each specific capture oligonucleotide sequence. A variety of pulsed laser diode sources that will be compatible with fluorophores, having good 2-photon cross-sections [100] in the wavelength range 375-450 nm, can also be used in the present invention. Suitable probes may be screened using tunable Ti:Sapphire laser excitation and using multiphoton microscopy.

For a bio-terrorism anthrax assay to be useful, it is necessary to detect B. anthracis DNA in environmental (real world) samples in which large amounts of DNA from other related and unrelated micro-organisms is likely to be present. Soil samples may be collected and the total DNA from the soil samples known to contain anthrax. DNA will be extracted using the Ultra Clean Soil DNA Kit (Mo Bio, Solano Beach, Calif.).

The present invention may be further applicable to DNA sequencing. While the human genome and other organisms have been sequenced [105,106], there is still a need for faster, cheaper and more sensitive DNA sequencing such as single strand sequencing [107]. This may be accomplished using an exonuclease to sequentially cleave single nucleotides from the strand, labeling them and detecting every one [107]. Such a process requires that every nucleotide must be both labeled and detected, which is even more difficult than single molecule detection, where one tries to find one fluorophore amongst many. Using intrinsic nucleotide fluorescence (enhanced by metal) would allow a new way to sequence DNA. Individual nucleotides are cleaved from a single strand of a polynucleotide and each of the free nucleotides is identified, based upon its characteristic fluorescence emission spectrum and lifetime. Alternatively, using the above detection method but no exonuclease cleavage, individual nucleotides of a single strand of a polynucleotide are identified by scanning a linear strand of the polynucleotide and obtaining a sequence directly from the intact DNA strand.

The assay of the present invention comprises a surface comprising silver colloids or islands. Attached to the surface and/or silver colloids/islands are polynucleotides which are complimentary to a target polynucleotide sequence. These capture polynucleotide sequences are attached at either the 5' or 3' end. The assay is performed by adding the target polynucleotide sequence to the assay surface and allowed to hybridize with the capture polynucleotides. Fluorophore-labeled capture polynucleotides are added and hybridize to the target polynucleotide. Unbound target polynucleotide and labeled capture sequence may be removed by washing, but washing is not required. Bound target polynucleotide is detected by metal enhanced fluorescence. The target polynucleotide sequence and capture sequence are preferably single stranded but may be double stranded and may be either deoxyribonucleic acid or ribonucleic acid. Many conditions suitable for hybridizing polynucleotides are known in the art. High stringency conditions or high stringency hybridization conditions are where polynucleotides are hybridized under the following conditions: 6×SSPE, 5× Denhardt's reagent, 50% formamide, 42° C., 0.5% SDS, 100 μg /ml sonicated denatured calf thymus or salmon sperm DNA. Medium stringency conditions or medium stringency hybridization conditions are where polynucleotides are hybridized under the following conditions: 6×SSPE, 5× Denhardt's reagent, 42° C., 0.5% SDS, 100 μg /ml sonicated denatured calf thymus or salmon sperm DNA. Low stringency conditions or low stringency hybridization conditions are where polynucleotides are hybridized under the following conditions: 6×SSPE, 5× Denhardt's reagent, 30° C., 0.5% SDS, 100 μg /ml sonicated denatured calf thymus or salmon sperm DNA. The formulae for the buffers used for hybridizations are: 20×SSPE: 3.6 M NaCl, 0.2 M phosphate, pH 7.0, 20 mM EDTA. 50× Denhardt's reagent: 5 g FICOLL Type 400, 5 g polyvinylpyrrolidone, 5 g bovine serum albumin and water to 500 ml.

It is recognized in the art of nucleotide hybridization that high, medium and low stringency hybridizations can be performed under a variety of different conditions. The provided conditions for performing nucleotide hybridizations are illustrative of the specific hybridizations for high, medium and low stringency conditions. These hybridization conditions are not intended to limit the disclosed method as one of ordinary skill in the art would recognize that the method of the instant invention is not dependent upon the disclosed hybridization conditions but can be achieved using many other different hybridization conditions.

Additionally, several different attached capture polynucleotide sequences may be used, as well as different fluorophore-labeled capture polynucleotide sequences to allow detection of more than one target polynucleotide sequence. Fluorophore-labeled capture polynucleotides of different sequences may be labeled with different fluorophores to allow identification of the different target sequences that may be present in a sample. The fluorophore-labeled capture polynucleotides may also comprise a silver colloid to further enhance fluorescence emission.

The capture immobilized DNA probe may be any length of nucleotides any preferably of a sufficient length of nucleotides to allow interaction of a bound fluorophore with the metallized surface of the substrate. The sequence may be from about 5 to about 300 nucleotides in

\*\*\*\*\*\*\*\*

While the invention has been described herein with reference to specific features, aspects and embodiments, it will be recognized that the invention may be widely varied, and that numerous other variations, modifications and other embodiments will readily suggest themselves to those of ordinary skill in the art. Accordingly, the ensuing claims are to be broadly construed, as encompassing all such other variations, modifications and other embodiments, within their spirit and scope.

REFERENCES

All references discussed herein are hereby incorporated herein by reference for all purposes.

[1] Shangkuan Y. H., Chang Y. H., Yang J. F., Linn H. C., and Shaio M. F. (2001). Molecular characterization of *Bacillus anthracis* using multiplex PCR, ERIC-PCR and RAPD, *Letts Appl. Microbiol.*, 32, 139-145.

[2] Lee M. A., Brightwell G., Leslie D., Bird H., and Hamilton, (1999). Fluorescent detection techniques for real-time multi strand specific detection of *Bacillus anthracis* using rapid PCR, *J. Appl., Microbio.*, 218-223.

[3] Berdal B. P., Mehl R., Haaheim H., Loksa M., Grunow R., Burans J., Morgan C., and Meyer H., (2000). Field detection of *Francisella tularenis* Scand. J. *Infect. Dis.*, 32, 287-291.

[4] Leroy E. M., Baize S., Lu C. Y., McCormick J. B., Georges A. J., Georges-Coubot M. C., Lansoud-Soukate J., and Fisher-Hoch S. P. (2000). Diagnosis of Ebola Haemorrhagic fever by RT-PCR in an epidemic setting, *J. Med. Virol.*, 60, 463-467.

[5] Makino S. I., Cheun H. I., Wateral M., Uchida I. and Takeshi K. (2001). Detection of anthrax spores from the air by real-time PCR, *Letts Appl. Microbiol.*, 33, 237-240.

[6] Stopa, P. J. (2000). The flow cytometry of *bacillus anthracis* spores revisited, *Cytometry*,41 ,237-244.

[7] Belgrader P., Young S., Yuan B., Primeau M., Christal L. A., Pourahmadi F., and Northrup M. A. (2001). A battery powered notebook thermal cycler for rapid multiplex real-time PCR analysis, *Anal. Chem.*, 73(2), 286-289.

[8] Mullis K. B. (1990). Target amplification for DNA analysis by the polymerase chain reaction, *Ann. Biol. Clin.*, 48(8), 579-582.

[9] Flelschmann M., Hendra P. J., and McQuillan A. J. (1974). Raman spectra of pyridine absorbed at a silver electrode, *Chem. Phys. Lett.*, 26(2), 163-166.

[10] Jeanmaire D. L. and Van Duyne R. P. (1997). Surface Raman spectroelectrochemistry. Part 1. Heterocyclic, aromatic and aliphatic amines adsorbed on the anodised silver electrode, *J. Electroanal. Chem.*, 84, 1-20.

[11] Aroca R., Jennings C., Kovacs G. J., Loutfy R. G. and Vincett P. S. (1985). Surface-enhanced Raman scattering of Langmuir-Blodgett monolayers of phthalocyanine by indium and silver island films, *J. Phys. Chem.*, 89, 4051-4054.

[12] Pettinger B., and Gerolymatou A. (1984). Dyes adsorbed at Ag-colloids: Substitution of fluorescence by similarly efficient surface fluorescence and surface Raman scattering, *Ber. Bungens. Phys. Chem.*, 88, 359-363.

[13] DeSaja-Gonzalez J., Aroca R., Nago Y. and DeSaja J. A. (1997). Surface enhanced fluorescence and SERRS spectra of N-octadecyl-3, 4:9, 10-perylenetetracarboxylic monohydride on silver island films, *Spectrochim. Acta.* Part A, 53, 173-181.

[14] Vo-Dinh T. (1998). Surface enhanced Raman spectroscopy using metallic nanostructures, *Trends in Anal. Chem.*, 17(8-9), 557-582.

[15] Axelrod D., Hellen E. H. and Fulbright R. M. (1992). Total internal reflection fluorescence, in Topics in Fiuorescence Spectroscopy, Vol. 3: *Biochemical applications*, (Lakowicz J. R., Ed.), Plenum Press, New York, pp. 289-343.

[16] Wokaun A., Lutz H.-P., King, A. P., Wild U. P. and Ernst R. R. (1983). Energy transfer in surface enhanced fluorescence, *J. Chem. Phys.*, 79(1), 509-514.

[17] Holland W. R. and Hall D. G. (1985). Waveguide mode enhancement of molecular fluorescence. *Optics Letts.*, 10(8), 414-416.

[18] Glass A. M., Liao P. F., Bergman J. G. and Olson D. H. (1980). Interaction of metal particles with adsorbed dye molecules: absorption and luminescence. *Optics Letts.*, 5(9), 368-370.

[19] Axelrod D., Burghardt T. P. and Thompson N. L. (1984). Total internal reflection fluorescence, *Ann. Rev. Biophys. Bioeng.*, 13, 247-268.

[20] Benner R. E., Domhaus R. and Chang R. K. (1979). Angular emission profiles of dye molecules excited by surface lasmon waves at a metal surface, *Optics Commun.*, 30(2), 145-149.

[21] Barnes W. L. (1998). Fluorescence near interfaces: The role of photonic mode density, *J. Modem Optics,* 45(4), 661-699.

[22] Camplon A., Gallo A. R., Harris C. B., Robota H. J. and Whitmore P. M. (1980). Electronic energy transfer to metal surfaces: A test of classical image dipole theory at short distances, *Chem. Phys. Letts.,* 73(3), 447-450.

[23] Sokolov K., Chumanov G. and Cotton T. M. (1998). Enhancement of molecular fluorescence near the surface of colloidal metal films, *Anal. Chem.,* 70, 3898-3905.

[24] Hayakawa T., Selvan S. T. and Nogami M. (1999). Field enhancement effect of small Ag particles on the fluorescence from $Eu^{3+}$-doped $SiO_2$ glass, Appl. *Phys. Lett.,* 74(11), 1513-1515.

[25] Selvan S. T., Hayakawa T. and Nogami M. (1999). Remarkable influence of silver islands on the enhancement of fluorescence from $Eu^{3+}$ ion-doped silica gels, *J. Phys. Chem. B.,* 103, 7064-7067.

[26] Lakowicz J. R. (2001). Radiative Decay Engineering: Biophysical and Biomedical Applications, *Anal. BioChem.,* 298, 1-24.

[27] Lakowicz J. R., Shen Y., D'Auria S., Malicka J., Fang J., Gryczynski Z. and Gryczynski I. (2002). Radiative Decay Engineering 2. Effects of silver island films on fluorescence intensity Lifetimes and Resonance energy transfer, *Anal. Biochem.,* 301, 261-277.

[28] Gryczynski I., Malicka J., Gryczynski. L, Geddes C. D. and Lakowicz J. R. (2002) The CFS engineers the intrinsic radiative decay rate of low quantum yield fluorophores, *J. FJuoescence,* 12(1), 11-13.

[29] Lakowicz J. R., Gryczynski I, Shen Y. B., Malicka J., and Gryczynski, Z, (2001). Intensified fluorescence, *Photonics Spectra,* 35(10), 96-104.

[30] Geddes C. D. and Lakowicz J. R. (2002). Metal-Enhanced Fluorescence, J. *Flourescence,* 12(2), 121-129.

[31] Strickler S. J. and Berg R. A. (1962). Relationship between adsorption intensity and fluorescence lifetime of molecules, *J. Chem. Phys.,* 37, 814-822.

[32] Sokolov K., Chumanov G., and Cotton T. (1998). Enhancement of molecular fluorescence near the surface of colloidal metal films, *Anal. Chem.,* 70, 3898-3905.

[33] Gersten J. L. and Nitzan A. (1985). Photophysics and Photochemistry near surfaces and small particles, *Surface Sci.,* 158, 165-189.

[34] Friedlander, A. M. (2000) in Current Clinical Topics in Infectious Diseases (eds. Reminton, J S. & Schwartz, M. N.) 335-349 (Blackwell Science, Inc, Malden, Mass., 2000).

[35] Pasteur L., Chamberlain C.-E. and Roux E. (1881). Compte rendu sommaire des experiences faites a Poilly-le-Fort, pres Melun sur la vaccination charbonneuse. Comptes *Rendus* des seances De *L'Academie des Sciences,* 92, 1378-83.

[36] Zilinska R. A. (1997). Iraq's biological weapons. J. Am. Med. Assoc., 278, 418-424.

[37] Tumbull P. C. B. (1999). Definitive indentification of *Bacillus anthracis*—a review. *J. Appl. Microbiology,* 87, 237-240.

[38] Keim P., Kalif k, Schupp J. Hill K, Travis S. E., Richmond K, Adair D. M., Hugh-Jones M., Kuske C. R. Jackson P. (1997). Molecular evolution and diversity in *Bacillus anthracis* as detected by amplified fragment length polymorphism markers. *J. of Bacteriology,* 3, 888-824.

[39] Keim P., Price L. B., Klevystka M., Smith K L, Schupp J.M., Okinaka R., Jackson P. J. and Hugh-Jones M. E. (2000). Multiple-locus variable number tandem repeat analysis reveals genetic relationships with *Bacillus anthracis. J. of Bacteriology,* 182, 2928-2936.

[40] Little S. F. and Ivins B. E. (1999). Molecular pathogenesis of *Bacillus anthracis* infection, *Microbes and Infection,* 2, 131-139.

[41] Kunst F. et al. (1997). The complete genome sequence of the gram positive bacterium *Bacillus subtilis. Nature,* 390, 249-56.

[42] Helgason E. et al. (2000). *Bacillus anthracis, Bacillus cereus,* and *Bacillus thuringiensis*~one species on the basis of genetic evidence. Appl Environ *Microbiol.,* 66, 2627-2630.

[43] Takami H. et al. (2000) Complete genome sequence of the alkaliphilic bacterium *Bacillus halodurans* and genomic sequence comparison with *Bacillus subtilis., Nucleic Acids Res.,* 28, 4317-4331.

[44] Aronson A. (2002). Sporulation and delta-endotoxin synthesis by *Bacillus thuringiensis, Cell Mol Life Sci.,* 59, 417-25.

[45] Okinaka R. T. et al. .(1999). Sequence and organization of pXO1, the large *Bacillus anthracis* plasmid harboring the anthrax toxin genes. J. Bacteriol., 181, 6509-6515.

[46] Okinaka R. et al. (1999). Sequence, assembly and analysis of pXO1 and pXO2, *J. Appl. Microbiol.,* 87, 261-262.

[47] Kuske C. R., Dunbar J., Andersen G., and Wilson W. (2002). Urban Environmental Backgrounds Characterization. Chemical and Biological National Security Program FY01 Annual Report, Technical Appendix.

[48] Thome C. B. (1993) in *Bacillus subtilis* and other Gram-Positive bacteria, 113-124, (American Society for Microbiology, Washington D.C.).

[49] Tumbull P. C., Hutson R. A., Ward M. J., Jones M. N., Quinn C. P., Finnie N. J., Duggleby C. J., Kramer J. M. and Melling J. (1992). *Bacillus anthracis* but not always anthrax,. *J. of Appl. Bacteriology,* 72 (1):21-8.

[50] Ramisse V., Patra G., Vaissaire J., and Mock M. (1999). The Ba813 chromosomal DNA sequence effectively traces the whole *Bacillus anthracis* community, *J of Appl. Microbiology,* 87, 22~228.

[51] Drexhage K. H. (1974). Interaction of light with monomolecular dye lasers in Progress in Optics, (Wolfe, E., Ed.), North Holland Publishing Company, Amsterdam, pp. 161-232.

[52] Amos R. M. and Barnes W. L. (1997). Modification of the spontaneous emission rate of $Eu^{3+}$ ions close to a thin metal mirror, *Phys. Rev. B.,* 55(11), 7249-7254.

[53] Huang Z, Lin C. C. and Deppe D. G. (1993). Spontaneous lifetime and quantum efficiency in light emitting diodes affected by a close metal mirror, IEEE J. *Quantum Electronics,* 29(12), 2940-2949.

[54] Amos R. M. and Barnes W. L. (1999). Modification of spontaneous emission lifetimes in the presence of corrugated metallic surfaces, *Phys. Rev. B.,* 59 (11), 7708~7714.

[55] Weltz D. A., Garrof S., Hanson C. D. and Gramila T. J. (1982) Fluorescent lifetimes of molecules on silver-island films, *Optics Letts.,* 7(2), 89-91.

[56] Michaels A. M., Jiang J. and Brus L. (2000). Ag nanocrystal junctions as the site for surface-enhanced Raman scattering of single Rhodamine 6G molecules, *J. Phys. Chem. B.,* 104, 11965-11971.

[57] Freeman R. G., Grabar K. C., Allison K. J., Bright R. M., Davis J. A., Guthrie A. P., Hommer M. B., Jackson M. A., Smith P. C., Walter D. G., and Natan M. J. (1995). Self-assembled metal colloid monolayers: An approach to SERS, Substrates. *Science,* 267 (17 March), 1629-1632.

[58] Ambrose W. P., Goodwin P. M., Jett J. H., Van Orden A., Werner J. H., and Keller R. A. (1999). Single molecule fluorescence spectroscopy at ambient temperature, *Chem. Rev.* 99, 2929-2956.

[59] Chen C. J. and Osgood R. M. (1983). *Phys. Rev. Lett*, 50, 1705-1708.

[60] Link S., and El-Sayed M. A. (2000). Shape and size dependence of radiative, non-radiative and photothermal properties of gold nanocrystals, *Int. Rev. Phys. Chem.*, 19(3), 409-453.

[61] Kumrnerlen J., Leitner A., Brunner H., Aussenegg F. R. and Wokaun A. (1993). Enhanced dye fluorescence over silver island films: Analysis of the distance dependence, *Molecular Phys.*, 80(5), 1031-1046.

[62] Garoff S., Weitz D. A., Alvarez M. S., and Gersten J. I. (1984). *J. Chem., Phys.*, 81(11), 5189-5200.

[63] Heavens O. S. (1955). *Optical properties of thin solid films*, Dover Publications, Inc., New York, pp. 261.

[64] Constantino C. J. L., Aroca R. F., Mendonca C. R., Mello S. V., Balogh D. T. and Oliveira Jr, O. N. (2001). Surface enhanced fluorescence and Raman imaging of Langmuir-Blodgett azopolymer films, *Spectrochemica Acta. A.*, 57, 281-289.

[65] Constantino C. J. L and Aroca R. F. (2000). Surface enhanced resonance Ramen scattering imaging of Langmuir-Blodgett monolayers of bis(benzimidazo)perylene on silver island films, *J. Ramen Spectrosc.*, 31, 887-890.

[66] DeSaja-Gonzalez J., Aroca R., Nagao Y. and DeSaja J. A. (1997). Surface enhanced fluorescence and SERRS spectra of N-octadecyl-3,4:9,10-prylenetetracarpoxylic monohydride on silver island films, *Spectrochemica Acta. A.*, 53, 173-181.

[67] DeSajaGonzalez J., Aroca R., Rodriguez-Mendez M. L., Souto J. and DeSaja J. A. (1998). Spectroscopic characterization and Langmuir-Blodgett films of N,N-bis(3-aminophenyl)3,4:9, 10- perylenebis(dicarboximide)$_1$ *Materials Science and Engineering C.*, 5, 297-299.

[68] Yang C. C., Josefowicz J. Y. and Alexandru L (1980). Deposition of ultrathin films by a withdrawal method, *Thin Sol. Films*, 74, 117-127.

[69] Bohme P., Vedantham G., Prvzybcien T. and Belfort G. (1999). Self-assembled monolayers on polymer surfaces: Kenetics, functionalisation and photopatleming$_1$ *Langmuir$_1$* 15, 532~5328.

[70] Rivas L., Sanchez-Cortes S., Garcia-Ramos J. V. and Morcillo G. (2001), Growth of silver colloidal particles obtained by citrate reduction to increase the Ramen enhancement factor, *Langmuir*, 17(3), 574-577.

[71] Shirtcliffe N., Nickel U. and Schneider S., (1999). Reproducible preparation of silver sols with small particle size using borohydride reduction:For use as nuclei for preparation of larger particles, *J. Colloid Interface Sci.*, 211(1), 122-129.

[72] Pastoriza-Santos I., and Liz-Marzan L. M. (2000). Reduction of silver nanopaiticles in DMF. Formation of mo~ers and stable colloids, *Pu'e AppL Chem.*, 72(1-2), ~90.

[73] Pastoriza~ntos I., Serra-Rodriguez C. and Liz44ar;~n L M. (2000). Self-assembly of silver particle monolayers on glass from Ag+ solutions in DMF, *J. Colloid Interface Sci.*, 221(2), 236-241.

[74] Bright R. M. Musick M. D. and Natan M. J. (1998). Preparation and characterization of Ag colloid monolayers, *Langmuir*, 14(20), 5695-5701.

[75] Ni F. and Cotton T. M. (1986). Chemical procedure for preparing surface-enhanced Raman scatterring active silver films, *Anal. Chem.*, 58(14), 3159-3163.

[76] Kreibig U. and Vollmer M. (1995). *Optical properties of metal clusters*, Springer, 532. pp.

[77] Link S. and El-Sayed M. A.(1999). Spectral properties and relaxation. dynamics of surface plasmon electronic oscillations in gold and silver nanodots and nanorods, *J. Phys. Chem. B.*, 103, 8410-8426.

[78] Kreibig U. and Genzel L (1985). *Optical absorption* of small metallic *particles, Surface Science*, 156, 678-700.

[79] Kreibig U., Gartz M. and Hilger A. (1997). Mie resonances: Sensors for physical and chemical cluster interface properties, *Ber. Bunsenges, Phys. Chem.*, 101(11), 1593-1604.

[80] Toshima N. and Yonezawa T. (1998). Bimetallic nanoparticles-novel materials for chemical and physical applications, *New J. Chem.*, 1179-1201.

[81] Caruso F., Caruso R. A. and Mohwald H. (1998). Nanoengineering of inorganic and hybrid hollow spheres by colloidal templating, Science, 282, 1111-1114.

[82] Freeman R. G., Grabar K. C., Allison K. J., Bright R. M., Davis J. A., Guthrie A. P., Hommer M. B., Jackson, M. A., Smith P. C., Walter D. G. and Natan M. J. (1995). Self Assembled metal colloid monolayers: An approach to SERS substrates, *Science*, 267, 1629-1632.

[83] Grabar K. C., Freeman R. G., Hommer M. B. and Natan M. J. (1995). Preparation and characterisation of Au colloid monolayers, *Anal. Chem.*, 67, 735-743.

[84] Yee J. K., Parry D. B., Caldwell K. D., and Harris J. M. (1991). Modification of quartz surfaces via thiol-disulphide interchange, *Langmuir*, 7, 307-313.

[85] Farmer S. C. and Patten T. E. (2000). Synthesis of luminescent organic/inorganic polymer nonocomposites, *Polym. Mater. Sci. Eng.*, 82, 237-238.

[86] Comor M. I. And Nedeljkovic J. M. (1999). Enhanced photo corrosion stability of colloidal cadmium sulphide-silica nanocomposites, *J. Mater. Sci. Let.i*, 18, 1583-1585.

[87] Lenigk R., Carles M., Ip N.Y. and Sucher N. J. (2001). Surface characterization of silicon-chip-based DNA microarray, *Langmuir*, 17, 2497-2501.

[88] Sabanayagam Ch. R., Smith C. L. and Cantor Ch. R. (2000). Oligonucleotide immobilization on micropatterned streptavidin surfaces, *Nucleic Acids Res.*, 28(8), 33.

[89] Okamoto T., Suzuki T., and Yamamoto N. (2000). Microarray fabrication with covalent attachment of DNA using bubble jet technology, *Nature Biotechnol.*, 18, 438-444.

[90] Mandal S., Gole A., Lala N., Gonnade R., Ganvitr V., and Sastry M. (2001). Studies on the reversible aggregation of cysteine-capped colloidal silver particles intercoonnected via hydrogen bonds, *Langmuir*, 17, 6262-6268.

[91] Lazarides A. A., and Schatz G. G. (2000). DNA-linked metal nanosphere materials. Structural basis for the optical properties, *J. Phys. Chem. B.*, 104, 460-467.

[92] Graham D., Smith W. E., Linacre A. M. T., Munro C. H., Watson N. D. and White P. C. (1997). Selective detection of deoxyribonucleic acid at ultralow concentrations by SERS, *Anal. Chem.*, 69, 4703-4707.

[93] Graham D., Mallinder B. J. and Smith W. E. (2000). Surface enhanced rosonance Raman scattering as a novel method of DNA discrimination, *Angew. Chem. Int. Ed.*, 39(6), 1061-1063.

[94] Lobmaier Ch., Hawa G., Goetzinger M., Wirth M., and Gabor F. (2001). Direct monitoring of molecular recognition processes using fluorescence enhancement at colloid coated microplates, *J. Molec., Recognit*, 14, 215-222.

[95] Gabor K. C., Freeman R. G., Hommer M. B. and Natan M. J. (1995). Preparation and characterization of Au colloid monolayers, *Anal. Chem.*, 67(4), 735-743.

[96] Sun Y.-P., Riggs J. E., Rollins H. W. and Guduru R. (1999). Strong Optical limiting of silver containing nanocrystaline particles in stable suspensions, *J. Phys. Chem. B.*, 103, 77-82.

[97] Xu C. and Webb W. W., (1997). Multiphoton excitation of molecular fluorophores and nonlinear laser microscopy, in *Topics in Fluoresence Specroscopy*, Vol, 5: *Nonlinear and two photon fluoresence*, (Lakowicz J.R., Ed.), Plenum Press, New York, pp.471-540.

[98] Diaspro A., (1999). Introduction of two-photon microscopy, *Microscopy Research and Technique,* 47, 163-164.

[99] Lakawicz J. R. and Gryczynski I., (1997). Multiphoton excitation of biochemical fluorophores, Topics in Fluorescence Spectroscopy Vol. 5: *Non-linear and Two-photon induced fluorescence* (Lakowicz J. R., Ed.), Plenum Press, New York, 5:87-144.

[100] Lakowicz J. R. (1999). Principles of Fluorescence Spectroscopy, (Lakowicz J. R., Ed.), Plenum Press, New York.

[101] Geddes C. D., Karolin J. and Birch D. J. S., (2002). 1 and 2-photon fluorescence anisotropy decay in silicon alkoxide sol-gels: Interpretation in terms of self-assembled nanoparticles, *Jn. Phys. Chem. B.,* 106(15), 3835-3841, 2002.

[102] Esumi K., Suzuki A., Yamahira A. and Torigoe K (2000). Role of poly(amidoamine) dendrimers for preparing nanoparticles of gold, platinum and silver, *Langmuir,* 16, 2604-2608.

[103] Welkos S. L, Lowe J. R., Eden-McCutchan F., Vodkin M., Leppla S. H., and Schmidt J. J. (1988). Sequence and analysis of the DNA encoding protective antigen of *Bacillus anthracis. Gene,* 69, 287-300.

[104] Baillie L. W. J. (2001) Thesis "The development of expression systems for the production of the Protective Antigen of *Bacillus anthracis*" Ph.D., University of Sheffield, UK.

[105] (2001)The Human Genome, *Nature,* February 15, 813-958.

[106] (2001) The Human Genome, *Science, February* 16, 1177-1351.

[107] Foldes-Papp Z., Angerer B., Ankenbauer W., and Rigler R. (2001). Fluorescent high-density labeling of DNA: error free substitution for a normal nucleotide, *J. Biotech.,* 86, 237-253.

That which is claimed is:

1. A method for detecting a *Bacillus anthracis* in a sample, the method comprising:
   a) providing a system consisting of:
      a layer of immobilized metal particles positioned on a surface substrate, wherein the immobilized metal particles have attached thereto a captured nucleotide sequence probe which is complementary to a known first nucleotide sequence section of a specific single nucleotide sequence of the *Bacillus anthracis*, wherein each capture nucleotide sequence probe is the same; and
      a free nucleotide sequence probe, wherein each free nucleotide sequence probe is the same, wherein the free nucleotide sequence probe is complementary to a known second nucleotide sequence section of the specific single nucleotide sequence of *B. anthracis* and has attached thereto a fluorophore, wherein the fluorophore is incorporated at a specific location on the free nucleotide sequence probe so that binding of the free nucleotide sequence probe to the known second nucleotide sequence section of the *B. anthracis* causes the fluorophore to be positioned from about 50 to about 500 Å from the surface of the immobilized metal particles;
   b) contacting the sample with the captured nucleotide sequence probe, wherein any *B. anthracis* in the sample having a nucleotide sequence complementary to the captured nucleotide sequence probe binds to the captured nucleotide sequence probe; and
   c) contacting any bound *B. anthracis* sequence with the free nucleotide sequence probe, thereby positioning the fluorophore for enhancing fluorescence emission when excited by an irradiating source and using such emissions to detect the presence of *B. anthracis*.

2. The method according to claim 1, wherein the metal particles are silver or gold.

3. The method according to claim 1, further comprising detecting fluorescence emissions with a detection device.

4. The method according to claim 3, wherein the detection device comprises a spectrometer, luminometer, plate reader, fluorescent scanner, or flow cytometer.

5. The method according to claim 1, wherein the captured nucleotide sequence probe is covalently linked to the immobilized metal particles.

6. The method according to claim 1, wherein binding of the captured and free nucleotide sequence probes to the first and second known nucleotide sequences of *B. anthracis* is conducted under highly stringent hybridization conditions.

7. The method according to claim 1, wherein the irradiating source uses a 1-photon or 2-photon excitation means.

8. The method according to claim 1, wherein the fluorophore comprises a low quantum yield species.

9. The method according to claim 1, wherein the fluorophore can undergo two-photon excitation.

10. The method according to claim 1, wherein the fluorophore is Rhodamine B, rose bengal or fluorescein isothiocyanate.

11. The method according to claim 1, wherein the free nucleotide sequence probe further comprises a metal colloid attached thereto and positioned for sandwiching the fluorophore between the metal colloid and the immobilized metal particles on the substrate when the known second nucleotide sequence of *B. anthracis* is bound.

12. An assay method for detecting a target pathogen in a sample, the method comprising:
   a) providing a system consisting of:
      an immobilized metallized layer positioned on a surface substrate, wherein the immobilized metallized layer has attached thereto an immobilized capture nucleotide sequence probe complementary to a first known nucleotide sequence of a specific single nucleotide sequence of the target pathogen, wherein each immobilized capture nucleotide sequence probe is the same having a specific length and sequence of nucleotides;
      a free nucleotide sequence probe, wherein each free nucleotide sequence probe is the same having a specific length and sequence of nucleotides, wherein the free nucleotide sequence probe is complementary to a second known nucleotide sequence of the specific single nucleotide sequence of the target pathogen, wherein the free nucleotide sequence probe has attached thereto a fluorophore, wherein the fluorophore is incorporated at a specific location on the free nucleotide sequence probe so that binding of the free nucleotide sequence probe to the nucleotide sequence of the target pathogen causes the fluorophore to be positioned from about 50 to about 500 Å from the immobilized metallized surface;

b) contacting the sample with the immobilized capture nucleotide sequence probe, wherein the nucleotide sequence of the target pathogen binds to the immobilized capture nucleotide sequence probe; and
c) contacting the bound nucleotide sequence of the target pathogen with the free nucleotide sequence probe; and
d) identifying the target pathogen by fluorescence emission by irradiating the system with an irradiating source to excite the fluorophore.

13. The method according to claim 12, wherein the target pathogen is *B. anthracis*.

14. The method according to claim 12, wherein the metallized surface comprises metal particles comprising silver or gold.

15. The method according to claim 12, further comprising detecting fluorescence emission with a detection device.

16. The method according to claim 15, wherein the detection device comprises a spectrometer, luminometer, plate reader, fluorescent scanner, or flow cytometer.

17. The method according to claim 12, wherein the irradiating source uses a 1-photon or 2-photon excitation means.

18. The method according to claim 12, wherein the fluorophore comprises a low quantum yield species.

19. The method according to claim 12, wherein the fluorophore can undergo two-photon excitation.

20. The method according to claim 12, wherein the fluorophore is Rhodamine B, rose bengal or fluorescein isothiocyanate.

21. The method according to claim 12, wherein the free nucleotide sequence probe further comprises a metal colloid attached thereto and positioned for sandwiching the fluorophore between the metal colloid and immobilized metal particles on the surface substrate when the nucleotide sequence of the target pathogen is bound to the immobilized metal particles.

* * * * *

UNITED STATES PATENT AND TRADEMARK OFFICE
CERTIFICATE OF CORRECTION

PATENT NO. : 8,114,598 B2
APPLICATION NO. : 10/536502
DATED : February 14, 2012
INVENTOR(S) : Chris D. Geddes et al.

It is certified that error appears in the above-identified patent and that said Letters Patent is hereby corrected as shown below:

On the Title Page, Item (73)

Please insert an additional Assignee:

--University of Maryland, Baltimore--

Signed and Sealed this
Sixth Day of August, 2013

Teresa Stanek Rea
*Acting Director of the United States Patent and Trademark Office*